US008765467B2

(12) United States Patent
Skorecki et al.

(10) Patent No.: US 8,765,467 B2
(45) Date of Patent: Jul. 1, 2014

(54) MULTICELLULAR COMPOSITIONS OF PLURIPOTENT HUMAN EMBRYONIC STEM CELLS AND CANCER CELLS

(75) Inventors: Karl L. Skorecki, Kiryat Shmuel (IL); Maty Tzukerman, Hagetaot (IL)

(73) Assignee: Technion Research and Development Foundation Ltd., Haifa (IL)

( * ) Notice: Subject to any disclaimer, the term of this patent is extended or adjusted under 35 U.S.C. 154(b) by 1833 days.

(21) Appl. No.: 10/555,537

(22) PCT Filed: May 5, 2004

(86) PCT No.: PCT/IL2004/000375
§ 371 (c)(1),
(2), (4) Date: Dec. 8, 2006

(87) PCT Pub. No.: WO2004/099364
PCT Pub. Date: Nov. 18, 2004

(65) Prior Publication Data
US 2007/0087435 A1    Apr. 19, 2007

(30) Foreign Application Priority Data

May 5, 2003    (IL) .......................................... 155783

(51) Int. Cl.
*A01N 1/00*    (2006.01)
*C12N 5/00*    (2006.01)
*C12N 5/07*    (2010.01)

(52) U.S. Cl.
USPC ............................. 435/347; 435/1.1; 435/325

(58) Field of Classification Search
USPC .......................................... 435/1.1, 325, 347
See application file for complete search history.

(56) References Cited

U.S. PATENT DOCUMENTS

| | | | |
|---|---|---|---|
| 5,166,065 A | 11/1992 | Williams | 435/377 |
| 5,453,357 A | 9/1995 | Hogan | 435/7.21 |
| 5,690,926 A | 11/1997 | Hogan | 424/93.1 |
| 5,753,506 A | 5/1998 | Johe | 435/377 |
| 6,146,888 A | 11/2000 | Smith | 435/325 |
| 6,200,806 B1 | 3/2001 | Thomson | 435/366 |
| 6,479,261 B1 | 11/2002 | Bauer | 435/69.52 |

FOREIGN PATENT DOCUMENTS

| | | | | |
|---|---|---|---|---|
| EP | 380646 | 8/1990 | ............ | A01K 67/00 |
| WO | WO01/00859 | 1/2001 | ............ | C12N 15/85 |
| WO | WO02/092756 | 11/2002 | | |
| WO | WO03/035851 | 5/2003 | ............ | C12N 5/00 |
| WO | WO03/066839 | 8/2003 | ............ | C12N 5/00 |

OTHER PUBLICATIONS

Wartgenberg et al., 2001, Faseb J., vol. 15, pp. 995-1005.*
Wartenberg et al.. 2001, FASEB J., vol. 15, pp. 995-1005.*
Fidler I.J., 2002, Differentiation, vol. 70, pp. 498-505.*
Hack et al., 2000, J Neuroscience Methods, vol. 95, pp. 177-184.*
Ma et al., Jan. 2003, Stem Cells, vol. 21, pp. 111-117.*
Mosammaparast et al., 2002, EMBO J., vol. 21(23), pp. 6527-6538.*
Bissell et al., 2001, Nature Reviews Cancer, vol. 1, pp. 46-54.*
Thomson et al., 1998, Science, vol. 282, pp. 1145-1147.*
Kurachi et al., 1994, Cancer, vol. 74(11), pp. 2984-2990.*
Olumi et al., 1999, Cancer Res., vol. 59, pp. 5002-5011.*
Fidler IJ, 2002, Differentiation, vol. 70, pp. 498-505.*
Richardson et al., 2001, Nature Biotech., vol. 19, pp. 1029-1034.*
Wartenberg et al., cited on IDS Dec. 14, 2006.*
Tzukerman M. et al., "An experimental platform for studying growth and invasiveness of tumor cells within teratomas derived from human embryonic stem cells". Proc Natl Acad Sci U S A. Nov. 11, 2003; 100(23):13507-12.
Walter-Yohrling J. et al., "Myofibroblasts enable invasion of endothelial cells into three-dimensional tumor cell clusters: a novel in vitro tumor model". Cancer Chemother Pharmacol. Oct. 2003;52(4):263-9.
Tumor-induced angiogenesis studied in confrontation cultures of multicellular tumor spheroids and embryoid bodies grown from pluripotent embryonic stem cells, Maria Wartenberg et al., *The FASEB Journal*, Apr. 2001, vol. 15.
Amit et al., "Clonally Derived Human Embryonic Stem Cell Lines Maintain Pluripotency and Proliferative Potential for Prolonged Periods of Culture", Developmental Biology 227, 271-278 (2000).
Kunz-Schughart et al., "A Heterologous 3-D Coculture Model of Breast Tumor Cells and Fibroblasts to Study Tumor-Associated Fibroblast Differentiation", Experimental Cell Research 266, 74-86 (2001).
Olumi et al., "Carcinoma-associated Fibroblasts Direct Tumor Progression of Initiated Human Prostatic Epithelium", Journal of Cancer Research, 59, 5002-5011 (1999).
Parrott et al., "Stromal-epithelial interactions in the progression of ovarian cancer: influence and source of tumor stromal cells". Molecular and Cellular Endocrinology 175, 29-39 (2001).
Javaherian et al., "Normal Keratinocytes Suppress Early Stages of Neoplastic Progression in Stratified Epithelium", Journal of Cancer Research, 58, 2200-2308 (1998).
Vogel, "Wisconsin to Dsitribute Embyonic Cell Lilnes", XP-001539914, Science, 287 (Feb. 2000).

* cited by examiner

*Primary Examiner* — Anoop Singh
*Assistant Examiner* — David A Montanari
(74) *Attorney, Agent, or Firm* — Browdy and Neimark, PLLC

(57) ABSTRACT

Methods are provided for producing novel multicellular compositions comprising cancer cells together with pluripotent human stem cells, which are capable of proliferating and differentiating into various normal cell lines and tissue structures. These novel multicellular compositions are useful for investigating the properties of cancer cells in a normal human tissue microenvironment, and for studying interventions that will modulate these properties including devising, testing and screening therapeutic drugs.

39 Claims, 6 Drawing Sheets

MULTICELLULAR COMPOSITIONS OF PLURIPOTENT HUMAN EMBRYONIC STEM CELLS AND CANCER CELLS

CROSS REFERENCE TO RELATED APPLICATIONS

This application is a 371 filing of International Application PCT/IL2004/000375 filed May 5, 2004 and published, in English, as International Publication No. WO 2004/099364 A2 on Nov. 18, 2004 and claims priority of Israel patent application no. 155783 filed May 5, 2003, which applications are incorporated by reference herein, in their entirety.

FIELD OF THE INVENTION

The present invention relates to multicellular compositions comprising cancer cells together with pluripotent human embryonic stem cells, in which the latter are capable of proliferating and differentiating into various normal cell lines. The invention further relates to methods of producing the multicellular compositions and to use of said multicellular compositions, inter alia in methods for drug screening and for evaluating the efficacy of cancer therapy.

BACKGROUND OF THE INVENTION

There is at present no readily available experimental system in which human cancer cells can be grown in the context of a mixed population of normal differentiated human cells. Such an experimental system would be advantageous for investigating responses to anticancer therapies and for exploring biological aspects of cancer cell growth (e.g. tumor cell invasion, angiogenesis, proliferation, migration and metastasis among others). Pluripotent human embryonic stem cells (hESC) are capable of differentiating into many distinct normal cell types, which makes them and their derivatives suitable candidates for research and medical applications.

U.S. Pat. No. 5,690,926 discloses non-murine pluripotential cells, including human pluripotential cells, that have the ability to be passaged in vitro for at least 20 passages and which differentiate in culture into a variety of tissues.

EP Patent No. 380646 discloses to the use of leukaemia inhibitory factor (LIF), in the isolation and propagation of embryonic stem cells in vitro.

U.S. Pat. No. 5,453,357 discloses a non-mouse pluripotential embryonic stem cell which can: (a) be maintained on feeder layers for at least 20 passages; and (b) give rise to embryoid bodies and multiple differentiated cell phenotypes in monolayer culture. The invention further provides a method of making a pluripotential embryonic stem cell comprising administering a growth enhancing amount of basic fibroblast growth factor, leukemia inhibitory factor, membrane associated steel factor, and soluble steel factor to primordial germ cells under cell growth conditions, thereby making a pluripotential embryonic stem cell.

U.S. Pat. No. 5,753,506 discloses a method of screening factors for the ability to promote the formation of embryonic stem cells, comprising combining primordial germ cells with a factor selected from the group consisting of fibroblast growth factor, leukemia inhibitory factor, membrane associated steel factor, and soluble steel factor with the factor to be screened and determining the formation of embryonic stem cells, whereas the formation of embryonic stem cells indicates a factor capable of promoting the formation of embryonic stem cells.

A method of enriching a population of mammalian cells for stem cells is disclosed in U.S. Pat. No. 6,146,888. The method comprises the steps of: providing in vitro a mixed population of mammalian cells whose genome comprises at least one nucleic acid construct encoding an antibiotic resistance gene operatively linked to a promoter which preferentially expresses said antibiotic gene in mammalian stem cells.

A method for culturing human embryonic stem cells in vitro for prolonged maintenance while preserving the pluripotent character of these cells, as well as a purified preparation of said cells, is disclosed in U.S. Pat. No. 6,200,806. It is further disclosed that these embryonic stem cells also retain the ability, throughout the culture and after continuous culture for eleven months, to differentiate into all tissues derived from all three embryonic germ layers.

A method for selective ex-vivo expansion of stem cells is disclosed in U.S. Pat. No. 6,479,261. The method comprises the steps of separating stem cells from other cells and culturing the separated stem cells in a growth media comprising a modified human interleukin-3 polypeptide having at least three times greater cell proliferative activity than native human interleukin-3, in at least one assay selected from the group consisting of: AML cell proliferation, TF-1 cell proliferation and methylcellulose assay.

A method of inducing angiogenesis in a tissue of a mammal, comprising the step of implanting a microorgan within the tissue of the mammal, is disclosed in International Publication No. WO 01/00859. The microorgan is derived from said mammal or from another mammal, wherein the organ may be selected from the group consisting of a lung, a liver, a kidney, a muscle, a spleen, a skin and a heart.

A genetically modified micro-organ explant expressing at least one recombinant gene product and methods for generating thereof, wherein the micro-organ explant comprises a population of cells and maintains a microarchitecture of an organ from which it is derived and at the same time having dimensions selected so as to allow diffusion of adequate nutrients and gases to cells in the micro-organ explant is disclosed in International Publication No. WO 03/035851

A population of hESC which under appropriate culture conditions differentiate into a substantially high percentage of insulin producing cells in spontaneously formed aggregated embryoid bodies is disclosed in International Publication No. WO02/092756 which is assigned to the applicant of the present invention.

Partially committed progenitors derived from embryonic stem cells that express telomerase and not being terminally differentiated and hence are capable of continued proliferation, are disclosed in International Publication No. WO 03/066839 which is assigned to the applicant of the present invention.

Nowhere in the background art is it taught or suggested that a multicellular compositions comprising human embryonic stem cells and cancer cells of human origin may be cocultured and moreover useful for drug screening.

SUMMARY OF THE INVENTION

The present invention provides multicellular compositions comprising pluripotent human embryonic stem cell together with human cancer cells wherein the stem cells maintain the ability to proliferate and to differentiate partially or fully, thereby forming a microenvironment of normal human tissue; and the cancer cells maintain their abnormal phenotype. In particular, the present invention provides three-dimensional structures comprising pluripotent human embryonic stem cells or differentiated cells derived from hESC in contact with human cancer cells. The cancer cells may be selected from established cell lines and primary cell cultures. The pluripotent stem cells can form embryoid bodies into which human cancer cells are introduced. Typically, embryoid bodies may be maintained in culture, or may be introduced into a suitable host animal. Within a suitable host animal embryoid bodies can give rise to teratomas. Accordingly, the cancer cells may be introduced either into the embryoid bodies or into the teratomas derived therefrom.

The present invention further provides methods for producing a multicellular composition comprising pluripotent stem cells and cancer cells, wherein the stem cells maintain the ability to proliferate and to differentiate partially or fully, thereby forming a microenvironment of normal human tissue; and the cancer cells maintain their abnormal phenotype.

The present invention further provides methods of screening therapeutic entities or modalities, including but not limited to anticancer drugs, immunotherapeutic drugs and agents for gene therapy, utilizing multicellular compositions comprising pluripotent stem cells together with cancer cells.

The present invention further provides methods for evaluating treatment efficacy of therapeutic agents, including but not limited to anticancer drugs, immunotherapeutic drugs and agents for gene therapy, utilizing multicellular compositions comprising pluripotent stem cells together with cancer cells.

The present invention is based in part on the unexpected finding that cancer cells of human origin that are grown within a teratoma derived from human embryonic stem cells, maintain their abnormal phenotype.

It is now disclosed for the first time that human cancer cells grown in vivo within a normal human microenvironment derived from human embryonic stem cells implanted in immunodeficient mice, invade the normal microenvironment and furthermore induce angiogenic activity within the normal human tissue. This induced angiogenic activity results in the generation of blood vessels of human origin.

According to one aspect, the present invention provides a multicellular composition comprising cancer cells within a microenvironment of normal human cells selected from the group consisting of: pluripotent human embryonic stem cells and normal human tissue derived from differentiated human embryonic stem cells; wherein the cancer cells maintain their abnormal phenotype.

It should be recognized that the present invention provides multicellular compositions, comprising human tumor cells growing within a human cellular microenvironment derived from differentiated human embryonic stem cells, in vitro and in vivo. In vitro, the multicellular composition of the invention comprises at least one embryoid body comprising cancer cells. In vivo, the multicellular composition of the invention comprises at least one teratoma comprising cancer cells.

According to one embodiment the present invention provides a multicellular composition comprising an embryoid body comprising human embryonic stem cells together with human cancer cells. According to another embodiment the present invention provides a multicellular composition comprising normal human tissue derived from differentiated human embryonic stem cells and cancer cells.

According to one embodiment the multicellular compositions are maintained in culture. According to another embodiment, the multicellular compositions are implanted within a host animal. According to some embodiments the multicellular compositions are implanted intraperitoneally and maintained in ascites form. According to some embodiments the multicellular compositions are implanted into a predetermined site within the host animal and develop into teratomas.

According to some embodiments the embryoid bodies are occluded within barrier membranes prior to implantation.

According to yet another embodiment the cancer cells of the multicellular composition of the present invention invade the normal human microenvironment derived from human embryonic stem cells.

According to yet another embodiment, the cancer cells induce angiogenic activity in the normal human microenvironment derived from human embryonic stem cells. According to yet another embodiment the cancer cells elicit formation of new human blood vessels within the normal human microenvironment derived from human embryonic stem cells. The human origin of the newly formed blood vessels may be verified using cell surface markers as are well known in the art.

According to yet another embodiment at least some cells in the multicellular composition comprise a construct comprising at least one exogenous polynucleotide. According to yet another embodiment, at least some cells in the multicellular composition comprise a vector comprising at least one exogenous polynucleotide. According to yet another embodiment, the vector is a plasmid or a virus. According to yet another embodiment, the vector is a virus selected from the group consisting of: adenoviruses, retroviruses and lentiviruses.

According to yet another embodiment, the exogenous polynucleotide is stably integrated into the genome of said at least some cells. According to yet another embodiment, the exogenous polynucleotide is transiently expressed by the at least some cells.

According to yet another embodiment, the construct further comprises at least one regulatory element. According to yet another embodiment, the at least one regulatory element is selected from the group consisting of: promoter, enhancer, post transcriptional element, initiation codon, stop codon, polyadenylation signal and selection marker. According to yet another embodiment, the exogenous polynucleotide is operably linked to expression control sequences.

According to yet another embodiment the cancer cells are transfected with a marker gene. According to yet another embodiment the cancer cells are stably transfected with a marker gene. According to certain exemplary embodiments, the marker is selected from a group consisting of: nuclear histone H2A-green fluorescent fusion protein (HEY-GFP), red fluorescent protein (RFP) with nuclear localization signal (NLS).

According to another aspect the present invention relates to methods of producing multicellular compositions in vitro and in vivo comprising normal human cells derived from human embryonic stem cells together with cancer cells. The methods comprise culturing hESC in conditions suitable for the formation of embryoid bodies or teratomas, which serve as an artificial microenvironment of normal human tissue for the cancer cells.

According to one embodiment the present invention provides a method for the formation of multicellular compositions comprising cancer cells of human origin within a normal human tissue derived from human embryonic stem cells, comprising:
(a) culturing hESC in conditions which promote formation of embryoid bodies;
(b) determining the formation of at least one embryoid body in the culture of (a);
(c) injecting cancer cells into the at least one embryoid body; and
(d) determining the presence of cancer cells within said at least one embryoid body.

According to another embodiment, the method further comprises:
(e) injecting said at least one embryoid body into a defined locus in a host animal.

According to another embodiment, the method further comprises:
(f) determining the formation of at least one teratoma in the locus of injection.

According to an alternative embodiment, step (e) comprises injecting said at least one embryoid body into the peritoneal cavity of a host animal.

According to an alternative embodiment, step (e) comprises injecting said at least one embryoid body into the host animal, wherein said at least one embryoid body is occluded within a barrier membrane prior to implantation.

According to yet another embodiment, the present invention provides a method for the formation of multicellular compositions comprising cancer cells of human origin within a normal human tissue derived from human embryonic stem cells, in vivo, comprising:
(a) injecting undifferentiated human embryonic stem cells into a host animal;
(b) determining the formation of at least one teratoma in the locus of injection;
(c) injecting cancer cells into the at least one teratoma of (b); and
(d) determining the presence of cancer cells within the at least one teratoma.

According to yet another embodiment, the undifferentiated human embryonic stem cells are injected into a defined locus in the host animal. According to yet another embodiment, the undifferentiated human embryonic stem cells are injected into the peritoneal cavity of a host animal. According to yet another embodiment, the undifferentiated human embryonic stem cells are occluded within a barrier membrane prior to implantation in a host animal.

According to certain alternative embodiments, the cancer cells are established cell lines or primary tumor cells. Preferably, the cancer cells are of a human origin. The cancer cells may be derived from solid malignant tumors, non-solid malignant tumors, and hematologic cancers. According to particular embodiments of the present invention the cancer cells may be selected from the group consisting of: prostate cancer, breast cancer, ovarian cancer, lung cancer, melanoma, renal cancer, bladder cancer, fibrosarcoma, hepatocellular carcinoma, osteocarcinoma, primary ductal carcinoma, giant cell sarcoma, ductal carcinoma, Hodgkin's disease, colorectal carcinoma, lymphoma, transitional cell carcinoma, uterine sarcoma, adenocarcinoma, plasmacytoma, epidermoid carcinoma, Burkitt's lymphoma, Ewing's sarcoma, gastric carcinoma, squamous cell carcinoma, neuroblastoma, rhabdomyosarcoma.

According to a yet another aspect, the present invention provides methods of screening therapeutic agents using a multicellular composition comprising cancer cells of human origin and normal human tissue derived from human embryonic stem cells, the method comprising contacting the multicellular composition with at least one candidate therapeutic agent, and determining its effect on the multicellular composition.

According to yet another embodiment, the present invention provides a method for screening, in vitro, the effect of a therapeutic agent on cancer cells comprising:
(a) culturing human embryonic stem cells in conditions which promote generation of embryoid bodies;
(b) determining the formation of at least one embryoid body in the culture of (a);
(c) injecting cancer cells into the at least one embryoid body;
(d) determining the presence of cancer cells within said at least one embryoid body;
(e) contacting said at least one embryoid body to a composition comprising a therapeutic agent; and
(f) determining whether the therapeutic agent has an effect on the at least one embryoid body.

According to yet another embodiment, determining the effect of the therapeutic agent on the at least one embryoid body comprises evaluating at least one of the following parameters: cell proliferation, cell differentiation, invasiveness of the cancer cells, angiogenesis and apoptosis.

According to yet another embodiment, the therapeutic agent is selected from the group consisting of: a cytotoxic compound, a cytostatic compound, anticancer drug, an antisense compound, an anti-viral agent, an agent inhibitory of DNA synthesis and function and an antibody.

According to one embodiment, the present invention provides a method of screening therapeutic agents, in vivo, comprising:
(a) injecting undifferentiated human embryonic stem cells into a host animal;
(b) determining the formation of at least one teratoma in the host animal;
(c) injecting cancer cells into the at least one teratoma;
(d) determining the presence of cancer cells within said at least one teratoma;
(e) treating the host animal having said at least one teratoma with a composition comprising a candidate therapeutic agent; and
(f) determining whether the therapeutic agent has an effect on said at least one teratoma.

According to an alternative embodiment, in step (a) the undifferentiated human embryonic stem cells are injected into the peritoneal cavity of a host animal.

According to yet another embodiment, treating the host animal is performed by topical administration of said therapeutic agent to said at least one teratoma.

According to certain alternative embodiment, the method comprises:
(a) culturing hESC in conditions which promote generation of embryoid bodies;
(b) determining the formation of at least one embryoid body in the culture of (a);
(c) injecting cancer cells into the at least one embryoid body thereby obtaining at least one multicellular composition;
(d) determining the presence of cancer cells within the at least one multicellular composition;
(e) injecting said at least one multicellular composition into a host animal;
(f) treating the host animal having said at least one multicellular composition with a therapeutic agent; and
(g) determining whether the therapeutic agent has an effect on said at least one multicellular composition.

According to an alternative embodiment, the at least at least one multicellular composition is injected into a site selected from a defined locus in said host animal and the peritoneal cavity of a host animal.

According to an alternative embodiment, step (e) comprises injecting into the host animal said at least one at least one multicellular composition, wherein said at least one at least one multicellular composition is occluded within a barrier membrane.

According to an alternative embodiment, step (g) comprises determining the effect of said at least one therapeutic agent on the multicellular composition.

According to yet another embodiment, treating the host animal is performed by intralesional administration of said therapeutic agent to the multicellular composition.

According to yet another embodiment, the therapeutic agent is conjugated to an agent selected from the group consisting of: imaging agent and a carrier.

According to yet another embodiment, the imaging agent is selected from, but not restricted to, paramagnetic particles: gadolinium, yttrium, lutetium and gallium; radioactive moieties: radioactive indium, rhenium and technetium; and dyes: fluorescin isothiocyanate (FITC), green fluorescent protein (GFP), cyan fluorescent protein (CFP), rhodamine I, II, III and IV, rhodamine B, and rosamine.

According to yet another embodiment, the therapeutic agent is an immunotherapeutic agent of human origin, selected from the group consisting of: an antibody or active fragments thereof, a cytokine, a chemokine, a polynucleotide encoding same and a cell of the immune system.

According to yet another embodiment, the therapeutic agent comprises at least one oligonucleotide, selected from antisense, sense nucleotide sequence, short interfering RNA, ribozyme and aptamer.

According to yet another aspect, the present invention provides a method for evaluating treatment efficacy of therapeutic agents, including but not limited to anticancer drugs, immunotherapeutic drugs and agents for gene therapy, utilizing multicellular compositions comprising normal human tissue together with cancer cells.

According to one embodiment, the present invention provides a method for evaluating treatment efficacy of therapeutic agents, comprising contacting a plurality of multicellular compositions with a therapeutic agent and assessing the damage caused by the therapeutic agent to the normal human tissue.

According to another embodiment, the present invention provides a method for evaluating treatment efficacy of therapeutic agents, comprising contacting a plurality of multicellular compositions with a therapeutic agent and assessing the damage caused by the therapeutic agent to the cancer cells.

According to yet another embodiment, the damage caused by the therapeutic agent is assessed by evaluating at least one of the parameters selected from the group consisting of: cell proliferation, cell differentiation, invasiveness of the cancer cells, angiogenesis and apoptosis.

According to yet another embodiment, the therapeutic agent is a cytotoxic compound selected from, but not restricted to, agents inhibitory of DNA synthesis and function selected from the group consisting of: adriamycin, bleomycin, chlorambucil, cisplatin, daunomycin, ifosfamide and melphalan; agents inhibitory of microtubule (mitotic spindle) formation and function: vinblastine, vincristine, vinorelbine, paclitaxel (taxol) and docetaxel; anti metabolites: cytarabine, fluorouracil, fluroximidine, mercaptopurine, methotrexate, gemcitabin and thioquanine; alkylating agents: mechlorethamine, chlorambucil, cyclophosphamide, melphalan and methotrexate; antibiotics: bleomycin and mitomycin; nitrosoureas: carmustine (BCNU) and lomustine; inorganic ions: carboplatin, oxaloplatin; interferon and asparaginase; hormones: tamoxifen, leuprolide, daunomycin, flutamide and megestrol acetate.

BRIEF DESCRIPTION OF THE DRAWINGS

The invention will be more fully understood and further advantages will become apparent when reference is made to the following detailed description of the invention and the accompanying drawings in which.

DETAILED DESCRIPTION OF THE INVENTION

Figure 1:
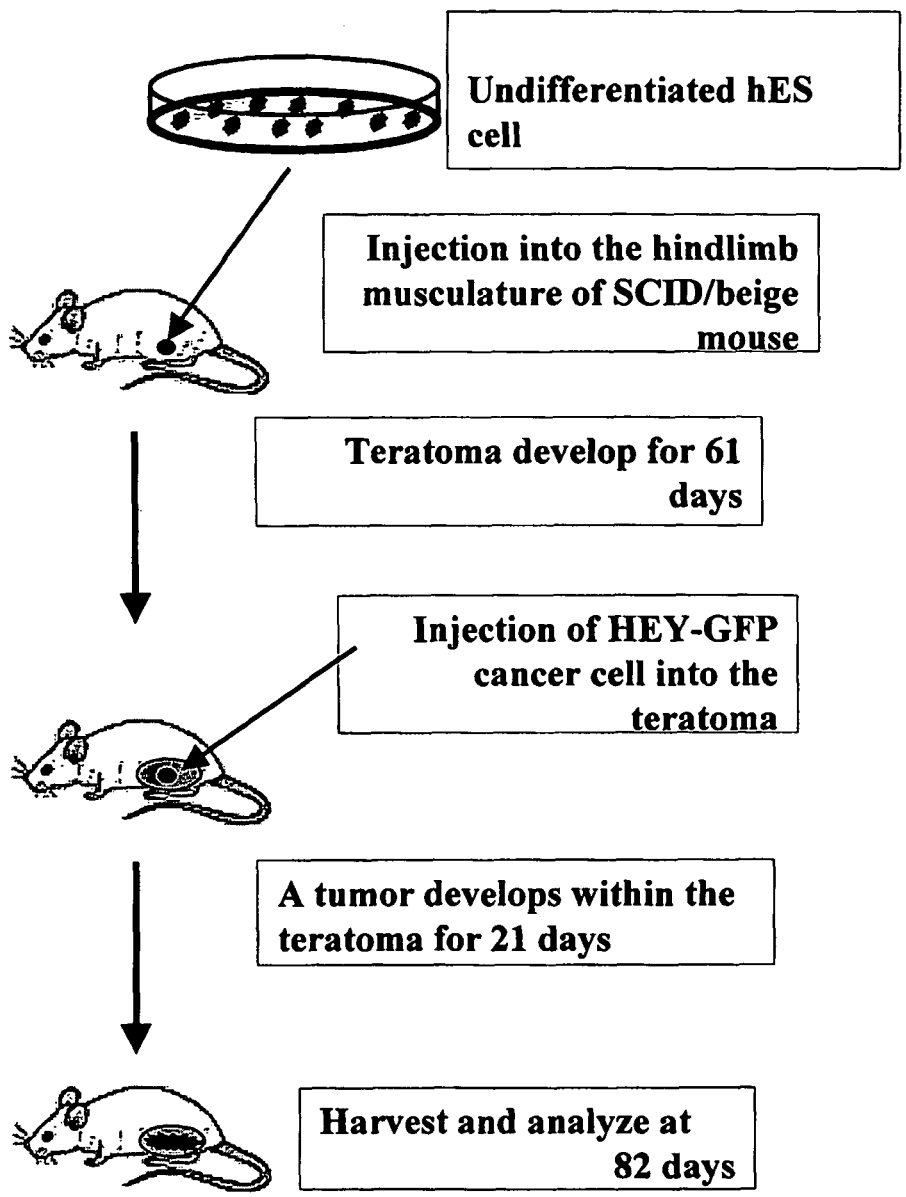
FIG. 1 presents a schematic presentation of a representative experimental protocol for developing cancer cells in teratomas within a host animal.

It has long been appreciated that the stroma surrounding tumor is frequently modified in terms of cellular composition and extracellular matrix during the course of tumor growth. Furthermore, tumor microenvironment has been shown to greatly influence tumorigenicity properties both at the site of the primary tumor and at metastastic sites. Thus for example, it has been demonstrated that human prostatic carcinoma-associated fibroblasts can promote carcinogenesis in human prostate epithelial cells which have been initiated, but which are not yet tumorigenic (Olumi et al., Cancer Res. 59: 5002-5011, 1999). Conversely, in the case of ovarian cancer cell lines, it was shown that tumor growth induced by injection of these cell lines in nude mice could be reduced by co-injection of normal bovine or human ovarian stromal cells, but not by co-injection of other stromal cell types (Parrott et al., Mol. Cell. Endocrinol, 175: 29-39, 2001). Interestingly however, the normal ovarian stromal cells did not appear to survive long-term incubation at the tumor site, which was instead supported by the recruitment of host murine stromal cells. Normal keratinocytes have also been shown to suppress early stages of neoplastic progression in skin epithelia (Javaherian et al., Cancer Res. 58:2200-2208, 1998).

The present invention provides an experimental platform for growth of human tumor cells within a microenvironment of normal human differentiated cells. Experimental system in which human cancer cells can be grown in the context of a mixed population of normal differentiated human cells may serve as an innovative platform for testing biological aspects of cancer cell growth (e.g. tumor cell invasion, angiogenesis) or response to anticancer therapies.

Numerous models have been previously developed for human tumorigenesis, for studying properties of tumor cells such as proliferation, migration, invasion, angiogenesis and metastasis among others, as well as for studying effects of anticancer treatments. Such models range from purely in vitro systems, such as monolayers or anchorage-independent growth in soft agar, to growth in vivo following subcutaneous, intramuscular, or intraperitoneal injection in immunocompromised mice (e.g. Kunz-Schughart et al., Exp Cell Res 2001 266:74-86). However, these experimental models of human tumor cell growth do not permit the study of properties of tumor cells related to their growth within the microenvironment of adjacent normal differentiated human cell tissues and structures and are not particularly amenable to the investigation of stromal interactions.

It was the emergence of in vivo models using tumor xenograft growth in immuno-compromised mice, which highlighted the importance of the stromal response. However, in the numerous published studies using this model, it has been the murine, rather than the human stromal response, which has been the target of investigation or experimental therapeutic intervention. Therefore, the present invention provides multicellular composites having a 3-dimensional microarchitecture, the composites comprising cancer cells of human origin together with a normal human microenvironment derived from human embryonic stem cells. Thus, the multicellular composites of the present invention perfectly simulate tumor tissue within normal tissue in human and may thus be used in a transitional platform between the pre-clinical and the clinical platforms for evaluating therapeutic ability of relevant candidates, particularly anticancer drug. In addition, the multicellular composites of the present invention enable studying the interactions between tumor cells and the surrounding microenvironment of differentiated human cell tissues and structures.

Upon successful introduction of cancer tissue or cells into a host animal, for example by injection or implantation, neovascularization is induced due to the angiogenic signals generated by the cancer cells. The resulting new blood vessels are established from cell, such as endothelial cells and smooth muscle cells, which are recruited from the host animal by the implanted cancer cells. The multicellular composition of the present invention comprise new blood vessel of human origin which are formed from human cells recruited from the normal human microenvironment of the multicellular compositions of the invention.

The ability to evaluate arrangement and content of cancer cells in the context of the normal tissue surrounding the cancer cells, using the system and method of the present invention, has an enormous experimental and clinical potential. For example, the system and method of the present invention may be used for elucidating properties and factors which modulate tissue invasion, reactive sclerosis, angiogenesis, and responses to certain anticancer regimens among others.

It should be recognized that the multicellular composites of the present invention, such as teratomas comprising cancer cells and embryoid bodies comprising cancer cells, may be designed to comprises a specific human tissue, such as a pancreatic tissue, and may also be designed as mixture of cells lack tissue homogeneity or organization.

The need for a system and method that enable monitoring arrangement and content of cancer cells in the context of the normal tissue surrounding the cancer cells is demonstrated by the following studies. Endostatin was shown to be a potent anti-angiogenic agent in tumors that were grown in immunocompromised mice (Folkman, Semin Oncol 6, Suppl 16, 15-18 2002). However, endostatin did not exhibit any inhibitory effect in human B-lineage acute lymphoblastic leukemia (B-ALL) that was engrafted within the marrow of immunodeficient mice (Eisterer et al, Molecular Therapy 5, 352-9, 2002). The results were non reproducible probably since in the first case the antiangiogenic agent, endostatin, was evaluated in a host animal and not in tumors grown in a microenvironment of human tissue comprising new blood vessels.

The system and method of the present invention are particularly advantageous for screening anticancer therapeutic compounds and compositions comprising thereof. The system and method provided in the present invention also allow to select anticancer therapeutic candidates that failed to perform anticancer activity when tested in the commonly used in vitro models or in vivo animal models known in the art.

Another advantage of the system and method is the ability to provide a suitable platform for evaluating the activity of anticancer and immuno-targeting therapeutic agents, which require for their activity a microenvironment of normal human tissue.

1. Preferred Modes for Carrying Out the Invention
1.1 Definitions

The term "embryonic stem cells" or "ESC" refers to pluripotent cells derived from the inner cell mass of blastocysts with the capacity for unlimited proliferation in vitro in the undifferentiated state (Evans et al., Nature, 292:154-6, 1981). Embryonic stem cells can differentiate into any cell type in vivo (e.g. Nagy, et al., Development, 110:815-821, 1990) and into a more limited variety of cells in vitro (e.g. Schmitt, et al., Genes and Development, 5: 728-740, 1991).

The term "adult stem cells" as used herein, refers to cells derived from differentiated human embryonic stem cells, and to multipotential adult progenitor cells (also known as MAPC; e.g. Nature 418:41-9, 2002) have extended replicative capacity and a restricted differentiation capacity (partial lineage commitment).

The term "embryoid body" as used herein, describes a population of ESC cells having a 3-dimensional microarchitecture. The population may comprise undifferentiated ESC and may further comprise differentiated ESC comprising the three major germ cell layers.

The term "teratoma" as used herein refers to a cellular complex having a 3-dimensional microarchitecture which develops from undifferentiated human embryonic stem cells implanted into a suitable animal host such as genetically immunocompromised mice. The teratoma comprises differentiated cell types which represent the major germline derived lineages. The teratoma comprises of derivatives of all three major germ cell layers (ectoderm, mesoderm, endoderm)

The term "multicellular system" as used herein refers to a cellular composition comprising human embryonic stem cells and cancer cells wherein the human embryonic stem cells are cultured in conditions suitable for differentiation and formation of embryoid bodies, in vitro, or teratomas, in vivo, thus generating a microenvironment of normal human tissue for the cancer cells injected therein. The terms "mixed culture", "coculture" and "multicellular system" may be used interchangeably.

The term "anticancer effect" as used herein, refers to a biological effect which can be manifested by a decrease in tumor size, a decrease in the number of metastases, an increase in life expectancy, or amelioration of various physiological symptoms associated with the cancerous condition. An "anticancer effect" can be manifested in the treatment of acute cancer as well as in cancer prophylaxis. A therapeutic agent that is capable of exerting an anticancer effect is termed herein an "an anticancer agent" or a "therapeutic agent".

1.2 Embryonic Stem Cells Culture

According to one embodiment, the present invention provides multicellular composition implanted within an immunocompromised animal, comprising cancer cells within a normal human tissue derived from differentiated human embryonic stem cells, wherein the cancer cells maintain their abnormal phenotype including the ability to induce angiogenic activity in the normal human tissue. Multicellular composition comprising cancer cells within a normal human tissue derived from differentiated human embryonic stem cells is described by the present inventors and coworkers and published after the priority date of the present application (Tzukerman et al., Proc. Natl. Acad. Sci. USA 2003 Nov. 11; 100 (23):13507-12, e-pub. 2003 Oct. 22).

The method of the present invention comprises utilization of embryonic stem cells capable of producing progenitors which can proliferate and differentiate into a desired population of committed precursors or into fully differentiated cells.

Preferably, the method of the present invention utilizes human embryonic stem cells which develop into teratomas when grown within immunocompromised mice.

Embryonic stem cells display the following characteristics:

1. Normal diploid karyotype.
2. Capacity for indefinite propagation in the undifferentiated state when grown on a feeder layer.
3. Telomerase enzyme activity in the undifferentiated state.
4. Formation of multicellular aggregates, yielding outgrowths containing multiple identifiable differentiated cell types, including derivatives of the three major germ cell layers (ectoderm, mesoderm, endoderm) upon release from the feeder layer.

Detailed procedures for culturing pluripotent human embryonic stem cells are known in the art, e.g. U.S. Pat. No. 6,280,718.

Methods for separating stem cells from dedicated cells are known in the art (e.g. U.S. Pat. No. 5,914,108).

Embryonic stem cells display the innate property to differentiate spontaneously. In order to enrich the population of the undifferentiated ESC of the invention and to maintain its homogeneity, the innate spontaneous differentiation of these cells has to be suppressed. Methods for suppressing differentiation of embryonic cells, particularly of human embryonic stem cells, may include culturing the undifferentiated embryonic cells on a feeder layer, such as of murine fibroblasts, also termed hereinafter "mouse embryonic fibroblasts" feeder layer or "MEFs", or in media conditioned by certain cells (e.g. U.S. Pat. No. 4,016,036).

MEF cells are commonly derived from day 12-13 mouse embryos in a medium consisting of DMEM supplemented with about 10% fetal bovine serum, about 2 mM 1-glutamine, and antibiotics, for example, 100 units/ml penicillin and 100 mg/ml streptomycin. MEF cells may be cultured on dishes, which are first coated with about 0.1% gelatin solution for one or more days in a 37° C./5% $CO_2$ incubator. The gelatin solution is then removed and the dishes are coated with irradiated MEF cells. The MEF cells may be irradiated with 5500 cGy from a cesium source prior to plating in the dish. The MEFs are added at a density of about $5·10^4$ cells/ml, 2.5 ml/well. The plates coated with MEFs are then placed in an incubator for one or more days until addition of human ES cells.

Human ES cells may be passed onto new MEFs, preferably at 3-8 day intervals, when cell density and morphologic appearance of differentiation is appropriate. The time of passage to a new MEF depends on cell density and morphologic appearance of differentiation. For passage, the medium in a well of hES cells is removed and medium containing about 1 mg/ml collagenase IV in DMEM is added.

Any cell culture media that can support the growth and differentiation of human embryonic stem cells, can be used with the present invention. Such cell culture media can include, but are not limited to Basal Media Eagle, Dulbecco's Modified Eagle Medium, Iscove's Modified Dulbecco's Medium, McCoy's Medium, Minimum Essential Medium, F-10 Nutrient Mixtures, OPTI-MEM® Reduced-Serum Medium, RPMI Medium, and Macrophage-SFM Medium or combinations thereof. The culture medium can be supplied in either a concentrated (e.g.: 10×) or non-concentrated form, and may be supplied as a liquid, a powder, or a lyophilizate. Culture media is commercially available from many sources, such as GIBCO BRL (MD, USA) and Sigma (MO, USA)

According to a certain embodiment, the medium for culturing nondifferentiated human embryonic stem cells may consist of 80% knockout Dulbecco's modified Eagle's medium supplemented with 20% serum replacement, 0.1 mM β-mercaptoethanol, 1% non-essential amino acid stock. Preferably, human recombinant basic fibroblast growth factor (bFGF) is added to the culture medium.

At the time of passaging the hESC to the MEF coated plates, if there are colonies of hES cells showing morphologic appearance of differentiation prior to cell passage, these colonies may be removed by gentle scraping with a pulled glass pipette. This is done with observation through a dissecting microscope. After removal of the differentiated cells, the remaining colonies may be passaged.

Alternatively, maintaining undifferentiated ESC in the laboratory, particularly mouse ESC, may be achieved by the addition of a differentiation inhibitory factor (commonly referred to as leukemia inhibitory factor or LIF) in the culture medium to prevent spontaneous differentiation (e.g. Pease, et al., Dev. Biol., 141: 344-352, 1990). LIF is a secreted protein and can be provided by maintaining embryonic stem cells on a feeder layer of cells that produce LIF (Robertson, Teratocarcinomas and Embryonic Stem Cells: A Practical Approach, Washington, D.C.: IRL Press, 1987) or by the addition of purified LIF (e.g. Pease, et al., Exp. Cell Res., 190: 209-211, 1990) to the medium in the absence of feeder layers.

International Patent Application WO 99/20741 describes methods and materials for growing pluripotent stem cells, including human embryonic stem cells, in the absence of feeder cells, on an extracellular matrix with a nutrient medium. Suitable are fibroblast matrices prepared from lysed fibroblasts or isolated matrix component from a number of sources. The nutrient medium may contain sodium pyruvate, nucleosides, and one or more endogenously added growth factors, such as bFGF, and may be conditioned by culturing with fibroblasts.

Differentiation of embryonic stem cells into a heterogeneous mixture of cells occurs spontaneously by removing the conditions which suppress differentiation, for example by removing MEFs or LIF, by generating a teratoma, or by other manipulations of the culture conditions (Gutierrez-Ramos, et al., Proc. Nat. Acad. Sci., 89: 9111-9175, 1992).

Differentiation pattern of embryonic stem cell may depend on the embryonic stem cell line and may even vary, in the same embryonic stem cell line, between different laboratories.

A method for selective ex-vivo expansion of stem cells is disclosed in U.S. Pat. No. 6,479,261. The method comprises the steps of separating stem cells from other cells and culturing the separated stem cells in a growth media comprising a modified human interleukin-3 polypeptide having at least three times greater cell proliferative activity than native human interleukin-3, in at least one assay selected from the group consisting of: AML cell proliferation, TF-1 cell proliferation and Methylcellulose assay. Methods for the treatment of a patient having a hemapoetic disorder are also disclosed in U.S. Pat. No. 6,479,261. These methods comprise removal of stem cells from a patient following ex-vivo selection of stem cells and expansion of the selected cells.

A method for obtaining Human hematopoietic stem cells by separating these cells from dedicated cells is disclosed in U.S. Pat. No. 5,914,108. The separated stem cells may than be maintained by regeneration in an appropriate growth medium.

A method to produce an immortalized mammalian ESC population is disclosed in U.S. Pat. No. 6,110,739. The method comprising: (a) transforming an embryonic stem cell population with an immortalizing gene to create a transformed stem cell population; (b) culturing said transformed stem cell population under effective conditions to produce a transformed embryoid body cell population; and (c) incubating said transformed embryoid body cell population under conditions suitable to obtain an immortalized cell population that differentiates into cellular lineages comprising primitive erythroid cells and definitive erythroid cells.

Methods for in vitro culturing of embryonic cell populations, particularly pluripotent human embryonic stem cells, utilizing combinations of growth factors for propagation and immortalization of these cells, are known in the art as for example disclosed in U.S. Pat. Nos. 5,690,926 and 6,110,739 and European Patent No. 380646, among many others.

An example for a purified preparation of pluripotent human embryonic stem cells is disclosed in U.S. Pat. No. 6,200,806. This preparation (i) will proliferate in an in vitro culture for over one year, (ii) maintains a karyotype in which the chromosomes are euploid and not altered through prolonged culture, (iii) maintains the potential to differentiate to derivatives of endoderm, mesoderm, and ectoderm tissues throughout the culture, and (iv) is inhibited from differentiation when cultured on a fibroblast feeder layer. The following cell surface markers characterize the purified preparation: SSEA-1 (−), SSEA-4 (+), TRA-1-60 (+), TRA-1-81 (+) and alkaline phosphatase (+).

Induction of differentiation in ES cells, preferably a controlled induction towards a specific cell lineage, is achieved for example by removing the differentiation-suppressing element, e.g. the feeder layer, from the culture. The embryonic stem cells may be placed in a culture vessel to which the cells do not adhere.

To effectively control the consequent differentiation, the cells must be in a homogeneous state. U.S. Pat. No. 6,432,711 provides a method for obtaining embryonic stem cells which are capable of differentiating uniformly into a specific and homogeneous cell line. The method comprises culturing embryonic stem cells under conditions which promote growth of the cells at an optimal growth rate. The embryonic stem cells then are cultured under conditions which promote the growth of the cells at a rate which is less than that of the optimal growth rate, and in the presence of an agent which promotes differentiation of the embryonic stem cells into the desired cell line. According to this method, a growth rate which is less than the optimal growth rate, is a growth rate from about 10% to about 80%, preferably from about 20% to about 50%, of the maximum growth rate for embryonic stem cells.

The desired cell types may be further enriched and/or purified using selection markers and gene trapping based on the methods disclosed in U.S. Pat. No. 5,602,301.

For example, the embryonic stem cells may be placed in a culture vessel to which the cells do not adhere. Examples of non-adherent substrates include, but are not limited to, polystyrene and glass. The substrate may be untreated, or may be treated such that a negative charge is imparted to the cell culture surface. In addition, the cells may be plated in methylcellulose in culture media, or in normal culture media in hanging drops. Media which contains methylcellulose is viscous, and the embryonic stem cells cannot adhere to the dish. Instead, the cells remain isolated, and proliferate, and form aggregates.

In a certain embodiment, the methods of the present invention utilize teratomas derived from differentiated human embryonic stem cells. Human embryonic stem cells when implanted into immunocompromised mice develop characteristic teratomas which contain numerous complex and multi-layered tissue structures, comprising differentiated cell types arising out of all the major germ line derived lineages.

Embryonic stem cell lines derived from human blastocysts have the developmental potential to form derivatives of all three embryonic germ layers even after prolonged culture.

In a certain alternative embodiment the multicellular composition of the present invention comprises the H-9.1 clone of undifferentiated human embryonic stems cells (Amit et al., *Dev. Biol.* 227, 271-8, 2000). After a prolonged culture this clone was shown to maintain the following characteristics: (1) active proliferation, (2) expression of high levels of telomerase, and (3) maintenance of normal karyotypes. High-passage of the H9.1 cells form teratomas in SCID-beige mice that include differentiated derivatives of all three embryonic germ layers. Other types of human embryonic stem cells may also be utilized to generate the multicellular systems of the present invention, for example, H1, H9, H9.2 and the like.

1.3 Multicellular Compositions and Formation Thereof.

According to one embodiment the present invention provides a multicellular composition comprising at least one embryoid body comprising human embryonic stem cells together with human cancer cells. According to another embodiment the present invention provides a multicellular composition comprising normal human tissue derived from differentiated human embryonic stem cells and cancer cells.

The multicellular compositions of the present invention comprise cancer cells. The cancer cells may be established cell lines or primary cells. Preferably, the cancer cells are of a human origin. The cancer cells may be derived from solid malignant tumors, non-solid malignant tumors, and hematologic cancers. Particular embodiments of the invention include cancer cells selected from the group consisting of:

prostate cancer, breast cancer, ovarian cancer, lung cancer, melanoma, renal cancer, bladder cancer, fibrosarcoma, hepatocellular carcinoma, osteocarcinoma, primary ductal carcinoma, giant cell sarcoma, ductal carcinoma, Hodgkin's disease, colorectal carcinoma, lymphoma, transitional cell carcinoma, uterine sarcoma, adenocarcinoma, plasmacytoma, epidermoid carcinoma, Burkitt's lymphoma, Ewing's sarcoma, gastric carcinoma, squamous cell carcinoma, neuroblastoma, rhabdomyosarcoma.

According to yet another embodiment the cancer cells of the multicellular composition of the present invention maintain the ability to at least one of the following: invade the normal human microenvironment, induce angiogenic activity in the normal human microenvironment, elicit formation of new human blood vessels within the normal human microenvironment The human origin of the newly formed blood vessels may be verified using cell surface markers as are well known in the art. For example, von Willebrand factor and smooth muscle cells-actin.

The multicellular compositions of the present invention may be generated in vitro or in vivo. According to one embodiment the multicellular compositions are maintained in culture. According to another embodiment, the multicellular compositions are implanted within a host animal. According to some embodiments the multicellular compositions are implanted intraperitoneally and maintained in ascites form. According to some embodiments the embryoid bodies are implanted into a predetermined site within the host animal and develop into teratomas. According to some embodiments the embryoid bodies are occluded within barrier membranes prior to implantation.

According to one embodiment the present invention provides a method for the formation of multicellular compositions comprising cancer cells of human origin within a normal human tissue derived from human embryonic stem cells, comprising:
  (a) culturing hESC in conditions which promote formation of embryoid bodies;
  (b) determining the formation of at least one embryoid body in the culture of (a);
  (c) injecting cancer cells into the at least one embryoid body; and
  (d) determining the presence of cancer cells within said at least one embryoid body.

According to another embodiment, the method further comprises:
  (e) injecting said at least one embryoid body into a defined locus in a host animal.

According to another embodiment, the method further comprises:
  (f) determining the formation of at least one teratoma in the locus of injection.

According to an alternative embodiment, step (e) is replaced with:
  (g) injecting said at least one embryoid body into the peritoneal cavity of a host animal.

According to an alternative embodiment, step (e) is replaced with:
  (h) injecting said at least one embryoid body into the host animal, wherein said at least one embryoid body is occluded within a barrier membrane prior to implantation.

According to some embodiment, human embryonic stem cells when implanted into immunocompromised mice develop characteristic teratomas which contain numerous complex and multi-layered tissue structures, comprising differentiated cell types arising out of all the major germ line derived lineages as described hereinabove.

According to some embodiments, cancer cells are injected into teratomas, in vivo, about 2 months after injection of the hESC into the immunodeficient mice.

According to yet another embodiment, the present invention provides a method for the formation of multicellular compositions comprising cancer cells of human origin within a normal human tissue derived from human embryonic stem cells, in vivo, comprising:
  (a) injecting undifferentiated human embryonic stem cells into a host animal;
  (b) determining the formation of at least one teratoma in the locus of injection;
  (c) injecting cancer cells into the at least one teratoma of (b); and
  (d) determining the presence of cancer cells within the at least one teratoma.

The presence of cancer cells within teratomas and within embryoid bodies is determined can take place a few days after injection of the cancer cells into the teratomas or the embryoid bodies. Preferably, the presence of cancer cells within a teratoma is determined a few weeks, 1 to 4 weeks, after injection of the cancer cells into the teratoma.

According to some embodiments, for the purpose of detection teratomas or embryonic bodies are harvested and prepared for histologic analysis. According to alternative embodiments, teratomas may be detected by an act of palpation or by imaging methods, preferably 2 to 7 weeks after injection.

According to alternative embodiments, the cancer cells are transfected with a green fluorescent reporter fusion protein (GFP), which enables to track them within the surrounding microenvironment of normal differentiated human cells and tissue. Thus, the presence of the cancer cells in a teratoma or in embryoid bodies is preferably achieved by exposing microsections of the teratoma or the embryoid bodies to anti GFP antibodies, and a suitable detection system.

The presence of cancer cells is typically monitored in a population of representative teratomas or embryoid bodies and is compared to the presence of cancer cells in control teratomas or embryoid bodies which did not receive an injection of cancer cells.

According to yet another embodiment, the undifferentiated human embryonic stem cells are injected into a defined locus in the host animal. According to yet another embodiment, the undifferentiated human embryonic stem cells are injected into the peritoneal cavity of a host animal. According to yet another embodiment, the undifferentiated human embryonic stem cells are occluded within a barrier membrane prior to implantation in a host animal.

According to certain embodiments, the hESC are initially cultured on 3-dimension polymer-based in vitro models (Levenberg et al., Proc. Natl. Acad. Sci. USA, 100:12741-12746, 2003) and the cancer cells are microinjected in the 3D structures formed within the 3-dimension polymer-based models.

Various means for injections of cells for the purpose of implantation within a suitable host animal are known in the art. Cells may be inoculated subcutaneously, intravenously, intramuscularly, intraperitoneally or inserted via other means of injection into the desired site of cells implantation. A preferred site for cell inoculation in immunocompromised mice is the hindlimb's muscle. An alternative method of implantation include use of barrier membranes which occlude the multicellular compositions and are then implanted in the host animal.

For the purpose of implantation using barrier membranes, hESC and the cancer cells are initially cultured in the presence of a barrier membrane. The barrier membrane may be commercial membranes and biocompatible membranes as known in the art (e.g. Teflon membranes, Resolut® LT and Biofix®). Preferably, the membrane are impermeable to certain cells, such as cells of the immune system and bacteria, and may be further impermeable to antibodies and other factors that can cause implant rejection. The membranes may be composed of a dense polymeric layer coupled with non-woven (e.g. Resolut® LT) or woven (e.g. Biofix®) fibers.

Several types of immunocompromised mice that are suitable for the teaching of the present invention are known in the art including different kinds of athymic nude mice and Severe Combined Immuno Deficient (SCID) mice. The multicellular composition of the present invention exemplified hereinbelow is implanted, by a way of non-limiting example, in SCID/beige mice.

1.4 Genetic Modifications

According to some embodiments, at least some of the cells of the multicellular compositions of the invention are genetically modified. According to some embodiments, the cancer cells, or at least some of the cancer cells, are genetically modified. According to other embodiments, the hESC, or at least some of the hESC, are genetically modified.

The genetically modified cells comprise a construct or a vector comprising at least one exogenous polynucleotide. The construct or the vector may further comprise at least one regulatory element. The at least one regulatory element may be selected from the group consisting of: promoter, enhancer, post transcriptional element, initiation codon, stop codon, polyadenylation signal and selection marker. The exogenous polynucleotide sequence may be operably linked to expression control sequences.

According to one embodiment, the exogenous polynucleotide is stably integrated into the genome of said at least some cells. Thus, the at least some transformed cells may constitutively express the exogenous polynucleotide. According to yet another embodiment, the exogenous polynucleotide is transiently expressed by the at least some cells.

The regulatory element may serve to confer functional expression of the exogenous polynucleotide. For example, expression of the exogenous polynucleotide may be produced by activating the regulatory nucleotide sequence.

According to some embodiments, the exogenous polynucleotide comprises a promoter sequence that controls the expression thereof. The promoter may be any array of DNA sequences that interact specifically with cellular transcription factors to regulate transcription of the downstream gene. The promoter may be derived from any organism, such as bacteria, yeast, insect and mammalian cells and viruses. The selection of a particular promoter depends on what cell type is to be used to express the protein of interest. Examples of the promoter include, but are not limited to, *E. coli* lac and trp operons, the tac promoter, the bacteriophage $\lambda \beta^P L$ promoter, bacteriophage T7 and SP6 promoters, β-actin promoter, insulin promoter, human cytomegalovirus (CMV) promoter, HIV-LTR (HIV-long terminal repeat), Rous sarcoma virus RSV-LTR, simian virus SV40 promoter, baculoviral polyhedrin and p10 promoter. The promoter may also be an inducible promoter that regulates the expression of downstream gene in a controlled manner, such as under a specific condition of the cell culture. Examples of inducible promoters include, but are not limited to, the bacterial dual promoter (activator/repressor expression system) which regulates gene expression in mammalian cells under the control of tetracyclines (Gossen et al., Proc. Natl. Acad. Sci. USA, 89, 5547-5551, 1992) and promoters that regulate gene expression under the control of factors such as heat shocks, steroid hormones, heavy metals, phorbol ester, the adenovirus EIA element, interferon, or serum.

According to another embodiment, the construct or vector comprise a selection marker. Selection markers are well known in the art, and the selection technique may vary depending upon the selection marker used. According to one embodiment, the selection marker is a gene inducing antibiotic resistance, enabling the survival of the transgenic cells in a medium containing the antibiotic as a selection agent. According to another embodiment, the selection marker is a reporter gene. The reporter gene can encode for a fluorescent protein, a chemiluminescent protein, a protein having a detectable enzymatic activity and the like, as is known to a person skilled in the art.

Genes that encode easily assayable marker polypeptides are well known in the art. In general, such gene are not present or expressed by the recipient organism or tissue and may encode a polypeptide whose expression is manifested by some easily detectable property, e.g. phenotypic change or enzymatic activity and thus when co-transfected into recipient cells with a gene of interest, provide a means to detect transfection and other events.

Among genes appropriate to use according to the present invention, are those that encode fluorescent proteins. Of interest are fluorescent compounds and proteins, such as naturally fluorescent phycobiliproteins. Also are the fluorescent proteins that are present in a variety of marine invertebrates, such as the green and blue fluorescent proteins, particularly the green fluorescent protein (GFP) of Aequorea Victoria and the red fluorescence protein (RFP) of Discosoma sp. The green fluorescent proteins constitute a class of chromoproteins found only among certain bioluminescent coelenterates. These accessory proteins are fluorescent and function as the ultimate bioluminescence emitter in these organisms by accepting energy from enzyme-bound, excited-state oxyluciferin (e.g., see Ward et al. Biochemistry 21:4535-40, 1982). Transfection of the cells may be transient or stable and may be applied with a vector that expresses the desired gene under the control of a promoter. The transient transfectants may also constitute the basis for selection of stable transfectants as exemplified herein below.

By way of a non-limiting example, the multicellular compositions may comprise HEY-ovarian cancer cells stably transfected so as to constitutively express a nuclear histone H2A-green fluorescent reporter fusion protein (HEY-GFP).

By way of another non-limiting example, the multicellular compositions may comprise HEY-ovarian cancer cells stably transfected so as to constitutively express red fluorescence protein (RFP) fused with three copies of the nuclear localization signal (NLS) of the simian virus 40 large T-antigen.

According to yet another embodiment, the multicellular compositions of the present invention comprise cancer cells that are transfected with a marker gene in order to enable detection of these cells within the multicellular compositions, particularly, to distinguish theses cancer cells from the normal environment using straight forward detection means. Marking the cancer cells of the compositions of the present invention, for example, with a fluorescent protein, is especially useful for determining the invasiveness of these cells within the normal human microenvironment.

Other methods may be applied to determine the presence of cancer cells in the systems of the present invention and to determine the invasiveness of these cells to the surrounding environment. For example, immunohistochemistry may be utilized with antibodies which bind epitopes specific to the cancer cells. Alternatively, in-situ hybridization with probes that bind mRNAs characteristic of the cancer cells may be used.

Introduction of synthetic polynucleotide into a target cell can involve one or more of non-viral and viral vectors, cationic liposomes, retroviruses, and adenoviruses such as, for example, described in Mulligan, R. C., (1993 Science 260: 926). Vectors are employed with transcription, translation and/or post-translational signals, such as targeting signals, necessary for efficient expression of the genes in various host cells into which the vectors are introduced. Such vectors are constructed and transformed into host cells by methods well known in the art. See Sambrook et al., Molecular Cloning: A Laboratory Manual, Cold Spring Harbor (1989).

Numerous methods for evaluating the effectiveness of transfection are known in the art. The effectiveness of transfection with a vector comprising an EGFP reporter gene may be monitored by straightforward fluorescence measurements as exemplified hereinbelow.

1.5 Methods for Screening Therapeutic Agents and Evaluating Efficacy Thereof

The experimental platforms known in the art for screening of anticancer therapeutic agents circumvents two major limitations, as follows:

(a) Loss of anticancer therapies at the phase I stage: A number of therapies, which have been tested in models based on experimental animals, have gone on for testing in phase I clinical trials. Unanticipated human cytotoxicity side effects in phase I clinical trials, have resulted in a high dropout percentage. In many cases, this dropout is a result of unanticipated cyto-toxicity to normal human tissues. Thus, use of the multicellular composition of the present invention for testing the efficacy of anticancer therapeutic agents may preempt the risk and expenditure related a phase I clinical trial, by revealing unanticipated untoward effects which may be only observed in when cancer cells are present in a normal human environment; and (b) Unwanted exclusion of anticancer therapies from proceeding to phase I trials: Currently, studies in experimental animals sometimes misleadingly yield results which preclude progression to human trials (such as the development of anti-angiogenic agents). However, it is known that untoward effects or toxicities in animal model systems may not be applicable to a human system. Nevertheless, untoward effects in an animal system are often the basis for precluding progression to a potentially informative set of clinical trials beginning with a phase I trial. Use of the multicellular composition of the present invention for testing therapeutic agents may offer and advantageous platform by showing that untoward effects or cytotoxic effects in experimental animals are not necessarily applicable in a human co-culture system.

Thus, the present invention provides multicellular systems of embryoid bodies or teratomas, which contain cancer cells therein. In effect, this generates a system in which a human cancer cell type of interest is growing in the context of mixed culture of differentiating and differentiated normal human cell types. This normal human microenvironment contains elements representing all of the different germline derivatives, including mature and immature fully differentiated structures. Thus, the interaction of the co-cultured cancer cells, which have been incorporated within the normal human microenvironment, can be subjected to experimental scrutiny, including for example, screening and determining the efficacy of chemotherapeutic agents, pro-apoptotic agents, anti-angiogenic agents, and a variety of established and novel anticancer therapies.

Use of multipotent neural stem cells and their progeny for the screening of drugs and other therapeutic agents is disclosed in U.S. Pat. No. 6,294,346. This patent disclosed a culture method for determining the effect of a therapeutic agent on multipotent neural stem cell progeny, wherein the multipotent neural stem cells are obtained from normal neural tissue or from a donor afflicted with a disease such as Alzheimer's Disease, Parkinson's Disease or Down's Syndrome. Additionally, a method of screening the effects of therapeutic agents on a clonal population of neural cells is provided. The technology provides an efficient method for the generation of large numbers of pre- and post-natal neural cells under controlled, defined conditions.

According to one embodiment, the present invention provides a method of screening therapeutic agents, in vivo, comprising:

(a) injecting undifferentiated human embryonic stem cells into a host animal;
(b) determining the formation of at least one teratoma in the host animal;
(c) injecting cancer cells into the at least one teratoma;
(d) determining the presence of cancer cells within said at least one teratoma;
(e) treating the host animal having said at least one teratoma with a composition comprising a candidate therapeutic agent; and
(f) determining whether the therapeutic agent has an effect on said at least one teratoma.

According to an alternative embodiment, the at least one embryoid body is injected into a site selected from a defined locus in said host animal and the peritoneal cavity of a host animal.

According to another alternative embodiment, step (a) is replaced with:

(g) injecting into a host animal undifferentiated human embryonic stem cells occluded within a barrier membrane.

According to yet another embodiment, treating the host animal is performed by topical administration of said therapeutic agent to said at least one teratoma.

According to certain alternative embodiment, the method comprises:

(a) culturing hESC in conditions which promote generation of embryoid bodies;
(b) determining the formation of at least one embryoid body in the culture of (a);
(c) injecting cancer cells into the at least one embryoid body;
(d) determining the presence of cancer cells within said at least one embryoid body;
(e) injecting said at least one embryoid body into a host animal;
(f) treating the host animal with a composition comprising a candidate therapeutic agent; and
(g) determining whether the candidate therapeutic agent has an effect on said at least one embryoid body.

According to an alternative embodiment, the at least one embryoid body is injected into a site selected from a defined locus in said host animal and the peritoneal cavity of a host animal.

According to an alternative embodiment, step (e) is replaced with:

(h) injecting into the host animal said at least one embryoid body, wherein said at least one embryoid body is occluded within a barrier membrane.

According to another embodiment, the after step (e) and before step (f) the method further comprises determining the formation of a teratoma from the at least one embryoid body.

According to an alternative embodiment, step (g) comprises determining whether said at least one therapeutic agent has an effect on the teratoma.

According to yet another embodiment, treating the host animal is performed by topical administration of said therapeutic agent to said at least one teratoma.

According to yet another embodiment, the present invention provides a method for screening, in vitro, the effect of a therapeutic agent on cancer cells comprising:
 (a) culturing human embryonic stem cells in conditions which promote generation of embryoid bodies;
 (b) determining the formation of at least one embryoid body in the culture of (a);
 (c) injecting cancer cells into the at least one embryoid body;
 (d) determining the presence of cancer cells within said at least one embryoid body;
 (e) contacting said at least one embryoid body to a composition comprising a therapeutic agent; and
 (f) determining whether the therapeutic agent has an effect on the at least one embryoid body.

According to yet another embodiment, determining the effect of the therapeutic agent on the multicellular composition comprises evaluating at least one of the following parameters: cell proliferation, cell differentiation, invasiveness of the cancer cells, angiogenesis and apoptosis.

According to another embodiment, the therapeutic agent is selected from the group consisting of: a cytotoxic compound, a cytostatic compound, anticancer drug, an antisense compound, an anti-viral agent, an agent inhibitory of DNA synthesis and function and an antibody.

According to yet another embodiment, the therapeutic agent is conjugated to an agent selected from the group consisting of: imaging agent and a carrier.

According to yet another embodiment, the imaging agent is selected from, but not restricted to, paramagnetic particles: gadolinium, yttrium, lutetium and gallinum; radioactive moieties: radioactive indium, rhenium and technetium; and dyes: fluorescin isothiocyanate (FITC), green fluorescent protein (GFP), cyan fluorescent protein (CFP), rhodamine I, II, III and IV, rhodamine B, and rosamine.

According to yet another embodiment, the therapeutic agent is an immunotherapeutic agent of human origin, selected from the group consisting of: an antibody, a cell of the immune system, such as a natural killer cell or a T-helper cell, a cytokine, a chemokine.

According to yet another embodiment, the therapeutic agent comprises at least one oligonucleotide, selected from antisense, sense nucleotide sequence, short interfering RNA, ribozyme and aptomer.

In recent years, advances in nucleic acid chemistry and gene transfer have inspired new approaches to engineer specific interference with gene expression.

Antisense technology has been one of the most commonly described approaches in protocols to achieve gene-specific interference. For antisense strategies, stochiometric amounts of single-stranded nucleic acid complementary to the messenger RNA for the gene of interest are introduced into the cell.

International Publication No. WO 02/10365 provides a method for gene suppression in eukaryotes by transformation with a recombinant construct containing a promoter, at least one antisense and/or sense nucleotide sequence for the gene(s) to be suppressed, wherein the nucleus-to-cytoplasm transport of the transcription products of the construct is inhibited. In one embodiment, nucleus-to-cytoplasm transport is inhibited by the absence of a normal 3' UTR. The construct can optionally include at least one self-cleaving ribozyme. The construct can also optionally include sense and/or antisense sequences to multiple genes that are to be simultaneously downregulated using a single promoter. Also disclosed are vectors, plants, animals, seeds, gametes, and embryos containing the recombinant constructs.

European Patent Application No. 0223399 A1 describes methods for the use of genetic engineering technology in plants to achieve useful somatic changes to plants, not involving the expression of any exogenous proteins, but instead controlling the expression of an endogenous protein or other DNA or RNA factor naturally introduced into the plant cells through outside agents, such as agents of disease or infection.

Antisense has recently become accepted as therapeutic moieties in the treatment of disease states. For example, U.S. Pat. No. 5,098,890 is directed to antisense oligonucleotide therapies for certain cancerous conditions. U.S. Pat. No. 5,135,917 provides antisense oligonucleotides that inhibit human interleukin-1 receptor expression. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenza virus. U.S. Pat. No. 4,806,463 provides antisense oligonucleotides and methods using them to inhibit HTLV-III (human T-cell lymphotropic virus type III, known also as HIV) replication. Antisense oligonucleotides have been safely administered to humans and several clinical trials of antisense oligonucleotides are presently underway. It is, thus, established that oligonucleotides can be useful therapeutic instrumentalities and that the same can be configured to be useful in treatment regimes for treatment of cells and animals, especially humans.

Aptamers are specifically binding oligonucleotides for non-oligonucleotide targets that generally bind nucleic acids. The use of single-stranded DNA as an appropriate material for generating aptamers is disclosed in U.S. Pat. No. 5,840,567. Use of DNA aptamers has several advantages over RNA including increased nuclease stability, in particular plasma nuclease stability, and ease of amplification by PCR or other methods. RNA generally is converted to DNA prior to amplification using reverse transcriptase, a process that is not equally efficient with all sequences, resulting in loss of some aptamers from a selected pool.

The methods of the invention may be further utilized for screening short interfering RNAs (siRNAs; Fire et al., Nature 391:806-811, 1998). RNA interference refers to the process of sequence-specific post-transcriptional gene silencing in animals mediated by siRNAs. The corresponding process in plants is commonly referred to as post-transcriptional gene silencing or RNA silencing. The process of post-transcriptional gene silencing is thought to be an evolutionarily conserved cellular defense mechanism used to prevent the expression of foreign genes and is commonly shared by diverse flora and phyla.

RNA interference is a phenomenon in which double stranded RNA (dsRNA) reduces the expression of the gene to which the dsRNA corresponds. The phenomenon of RNAi was subsequently proven to exist in many organisms and to be a naturally occurring cellular process. The RNAi pathway can be used by the organism to inhibit viral infections, transposon jumping and to regulate the expression of endogenous genes (e.g. Zamore PD., Nat Struct Biol. 8(9):746-750, 2001).

International Publication No. WO 00/01846 discloses methods for identifying specific genes responsible for conferring a particular phenotype in a cell using specific dsRNA molecules. International Publication No. WO 01/29058 discloses specific genes involved in dsRNA-mediated RNAi. International Publication No. WO 99/07409 discloses specific compositions consisting of particular dsRNA molecules combined with certain anti-viral agents. International Publication No. WO 99/53050 discloses certain methods for decreasing the phenotypic expression of a nucleic acid in plant cells using certain dsRNAs. International Publication No. WO 01/49844 discloses specific DNA constructs for use in facilitating gene silencing in targeted organisms.

International Publications Nos. WO 02/055692, WO02/055693, and EP 1144623 B1 disclose methods for inhibiting gene expression using RNAi. International Publications Nos. WO 99/49029 and WO01/70949, and AU 4037501 describe certain vector expressed siRNA molecules. U.S. Pat. No. 6,506,559, discloses methods for inhibiting gene expression in vitro using certain siRNA constructs that mediate RNAi. U.S. Pat. No. 5,681,747 discloses methods for inhibiting human-PKCα expression with an oligonucleotide specifically hybridizable to a portion of the 3'-untranslated region of PKCα.

According to yet another embodiment, the effect of said therapeutic agent on the at least one teratoma is evaluated by way of comparison to the effect exerted by said therapeutic agent on at least one other teratoma generated by the teaching of the present invention and which is essentially similar to the at least one teratoma, wherein the at least one other teratoma is implanted in a non-treated suitable host animal. According to yet another embodiment, the effect of said therapeutic agent on the at least one teratoma is evaluated by way of comparison to the effect exerted by said therapeutic agent on cancer cells that are implanted in the same or different host animal directly and not within teratomas.

According to yet another embodiment, determining the effect of the therapeutic agent on the multicellular composition comprises evaluating at least one of the following parameters: cell proliferation, cell differentiation, invasiveness of the cancer cells, angiogenesis and apoptosis on the arrangement and content of cancer cells.

According to yet another aspect, the present invention provides a method for evaluating treatment efficacy of therapeutic agents, including but not limited to anticancer drugs, immunotherapeutic drugs and agents for gene therapy, utilizing multicellular compositions comprising normal human tissue together with cancer cells.

According to one embodiment, the present invention provides a method for evaluating treatment efficacy of therapeutic agents, comprising contacting a plurality of multicellular compositions with a therapeutic agent and assessing the damage caused by the therapeutic agent to the normal human tissue.

According to another embodiment, the present invention provides a method for evaluating treatment efficacy of therapeutic agents, comprising contacting a plurality of multicellular compositions with a therapeutic agent and assessing the damage caused by the therapeutic agent to the cancer cells.

According to yet another embodiment, the damage caused by the therapeutic agent is assessed by evaluating at least one of the parameters selected from the group consisting of: cell proliferation, cell differentiation, invasiveness of the cancer cells, angiogenesis and apoptosis.

According to yet another embodiment, the therapeutic agent is a cytotoxic compound selected from, but not restricted to, agents inhibitory of DNA synthesis and function selected from the group consisting of: adriamycin, bleomycin, chlorambucil, cisplatin, daunomycin, ifosfamide and melphalan; agents inhibitory of microtubule (mitotic spindle) formation and function: vinblastine, vincristine, vinorelbine, paclitaxel (taxol) and docetaxel; anti metabolites: cytarabine, fluorouracil, fluroximidine, mercaptopurine, methotorexate, gemcitabin and thioquanine; alkylating agents: mechlorethamine, chlorambucil, cyclophosphamide, melphalan and methotrexate; antibiotics: bleomycin and mitomycin; nitrosoureas: carmustine (BCNU) and lomustine; inorganic ions: carboplatin, oxaloplatin; interferon and asparaginase; hormones: tamoxifen, leuprolide, flutamide and megestrol acetate.

According to yet another embodiment, the therapeutic agent is an anti-tumor agent, including, but not limited to, daunomycin.

According to some embodiments, the damage caused by the therapeutic agent to the plurality of multicellular compositions is assed with reference to a plurality of untreated multicellular compositions and with reference to the plurality of multicellular compositions before treatment with the therapeutic agent.

The multicellular compositions may be maintained and treated with the therapeutic agent in vitro and in vivo. In the latter, the treatment may be administered locally or administered systemically, for example, by intravenous injection.

2. Other Applications Having established the feasibility of the experimental platform, a broad array of applications to cancer research can be undertaken, ranging from very basic cell biological studies of biochemical and signaling interactions between different types of tumors and surrounding human differentiated cells to pre-clinical testing of anti-cancer agents targeted to disable the human neo-angiogenic response. Among others, such applications include:

Genetic manipulation of cytokine, growth factor, and enzyme systems in the tumor cells, or in the human embryonic stem cells from which the differentiated microenvironments are derived. In previous tumor xenograft studies, such genetic manipulations have been carried out by transgenic modulation of the host mouse (Huang et al., 2002) rather than within differentiated human cells.

Extrapolation to human tumor cells freshly harvested from clinical samples.

Fractionation from within the bulk tumor population of specific subpopulations of cells with characteristic gene expression profiles or surface markers associated with tumorigenic properties of interest.

Pre-clinical testing of anti-angiogenic, immunotargeting or other therapeutic anti-cancer agents and drugs whose properties might be different within the context of a human differentiated cellular microenvironment.

Numerous additional applications can be considered for the multicellular systems of the present invention. Among others, these include quantitation of tumor proliferation following in vivo pulse labeling with BrdU, comparative quantitation of angiogenic responses, and comparison of properties related to local microenvironment among different human tumor cell types, including tumor cells harvested from clinical primary samples.

The multicellular composition of the present invention in a suitable host animal may be further utilized for exploring aspects related to the interaction between the cancer cells the immune systems such as:
1. Therapeutic anticancer effects of the immune system.
2. The influence of the normal microenvironment which surrounds the cancer cells on the efficacy of the therapeutic activity of the immune system.

3. Interactions between cells of the immune system cells and cancer cells, for example, infiltration of T cells into tumors.
4. The influence of immunological factors such as cytokines and chemokines on the migration of tumor-specific T cells and their activity.

The following examples are to be construed in a non-limitative fashion and are intended merely to be illustrative of the principles of the invention disclosed.

EXAMPLES

Materials and Methods

Cell Culture.

The human undifferentiated embryonic stem cell clone H9.1 (Itskovitz-Eldor et al. *Mol Med.* 6, 88-95, 2000) were grown on mitomycin C treated mouse embryonic fibroblasts (MEF) feeder layer as previously described (Tzukerman et al. *Mol Biol Cell* 11, 4381-91, 2000). The HEY cell line that was initiated from a disaggregated xenograft ovarian tumor (Braunstein et al., *Cancer Res.* 61, 5529-36 2001) was grown in RPMI 1640 supplemented with 10% FCS and 1% L-glutamine (Biological Industries, Israel).

Reporter Plasmid and Stable Transfection.

The cDNA coding region for the green fluorescence protein (GFP) fused downstream to the histone H2A (Zur et al., *EMBO J.* 21, 4500-10, 2002) was inserted into AgeI and NotI restriction sites of the pEGFP-N1 expression vector (Clontech). Stable transfection of HEY cells was carried out using FuGENE6™ reagent (Roche) and 300 µg/ml G418 (Life Technologies™) for selection of stable clones.

Teratoma Formation.

Undifferentiated hES cells were harvested using 1 mg/ml collagenase type IV (Life Technologies™) and injected into the hindlimb of SCID/beige mice (~5×10$^6$ cells per injection). Teratomas were palpable after 4 weeks. At 61 days following initial injection of H9.1 cells, 10$^6$ HEY-GFP cells were injected into the teratoma and permitted to grow for an additional 21 days. Control non-injected teratomas, HEY-GFP injected teratomas, as well as tumor nodules derived from direct injection of HEY-GFP, were all harvested at 82 days.

Histological Analysis.

Teratomas were harvested, fixed for 48 h in 10% neutral buffered formalin, transferred into 70% ethanol and processed using a routine wax embedding procedure for histologic examination. 6-µm paraffin sections were mounted on Super FrostPlus® microscope slides (Menzel-Glaser, Germany) and stained with hematoxylin/eosin.

Immunohistochemistry.

Sides were deparaffinized using xylene and rehydrated through a series of gradients of alcohol to water. Antigens were retrieved using microwave exposure at 90° C. for 8 minutes in a citrate buffer pH6.1. Endogenous peroxidase enzyme activity was blocked using 3% hydrogen peroxidase in methanol for 30 minutes at room temperature. Slides were washed in distilled water and in PBS pH7.4 and then were blocked using 10% non-immuned goat serum (GFP—for 1 hour, CD31 and CD34—for 24 hours at 4° C.). Slides were incubated for 24 hours at 4° C. with the primary antibodies: rabbit polyclonal anti GFP-1:2000 (Molecular Probes), mouse monoclonal anti human CD34-1:50 (DAKO), rabbit polyclonal anti mouse CD31 1:2000, followed by incubation with goat anti-rabbit or anti-mouse biotinylated secondary antibody. Pre-immune rabbit or mouse sera were used as negative controls. Detection was accomplished using Histostain-SP (AEC) kit (Zymed Lab). Counterstaining was carried out using hematoxylin.

Example 1

In Vitro Culture of Pluripotent Human Embryonic Stem Cells

Large stocks of primary MEFs were prepared as described by Robertson (Robertson E. G. Ed., Teratocarcinomas and embryonic stem cells: a practical approach in Practical approach series, IRL Press 1987, 71-112) and stored in liquid nitrogen. After each thaw, cells were used for only 3-5 passages. The human ES-H9 cells were maintained in the undifferentiated state by propagation in culture on a feeder layer of MEFs that was mitotically inactivated by gamma irradiation with 35 Gy and plated on gelatin-coated six-well plates.

Cells were grown in knockout Dulbecco's modified Eagle's medium (Gibco, Grand Island, N.Y.) supplemented with 20% serum replacement (Gibco), 1% nonessential amino acids (Gibco), 0.1 mM 2-mercaptoethanol (Gibco), 1 mM glutamine (Biological Industries, Bet-Haemek, Israel), 4 ng/ml human bFGF (PeproTech, Rocky Hill, N.J.). Cells were cultured in 5% $CO_2$, 95% humidity and were routinely passaged every 4-5 days after disaggregation with 0.1% collagenase IV (Gibco).

Methods for the induction of induction of hES differentiation were applied (e.g. Keller in Curr. Op. Cell Biol. 7:862, 1995). About 10$^7$ undifferentiated hES cells were disaggregated and cultured in suspension in 100-mm bacterial-grade petri dishes (Greiner, Frickenhausen, Germany), which resulted in induction of synchronous differentiation characterized by initial formation of small aggregates and followed by the acquisition of the configuration of embryoid bodies.

Alternatively, hES colonies were left unpassaged until confluence (10 days) and were replated on gelatinized six-well tissue culture plates in the absence of a feeder layer. The cells spontaneously differentiated to an array of cell phenotypes. The growth media used in differentiation were as described above.

Example 2

Development of Human Cancer Cells Within Teratomas

To determine whether human cancer cells injected into mature and well-developed teratomas growing in immuno-compromised mice, would grow within the teratoma and whether they would display properties associated with malignancy such as invasiveness and recruitment of blood vessels from the teratoma HEY-ovarian cancer cells (Buick et al., *Cancer Res.* 45, 3668-76, 1985) were used. These cells have been stably transfected so as to constitutively express a nuclear histone H2A-green fluorescent reporter fusion protein (HEY-GFP), which enables to track them within the surrounding microenvironment of normal differentiated human cells and tissue.

Figure 2A:
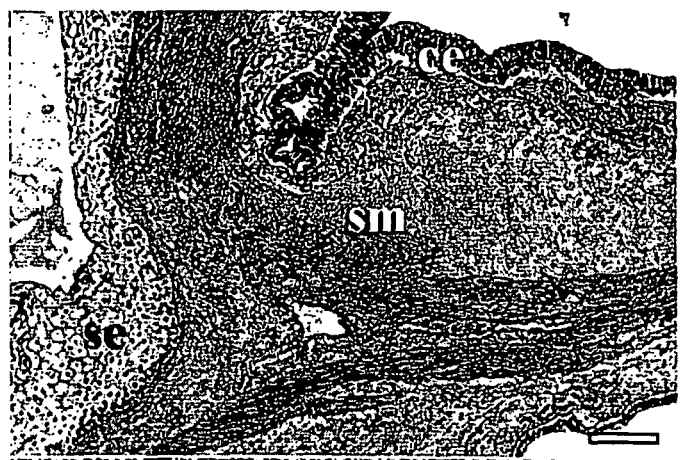
FIG. 2 is photomicrographs of teratoma, tumor and boundary region using reticulin staining with Gomori technique showing: (A) Typical appearance of teratoma derived structure in SCID/beige mice, with derivatives of three embryonic germ layers [se: stratified epithelium of ectodermal origin, m: smooth muscle of mesodermal origin, ce: columnar epithelium with goblet cells of endodermal origin]; (B) Homogeneous mass of HEY ovarian carcinoma tumor cells (tu); and (C) Boundary region of tumor cells (tu) adjacent to a differentiated teratoma structure consisting of a neurovascular bundle with a venule (v) arteriole (a) and a nerve (n). Bar=200 µm in all three panels.
Figure 2B:
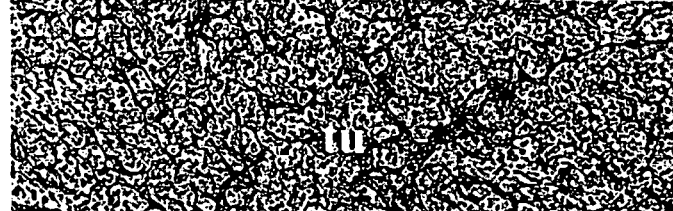
Figure 2C:
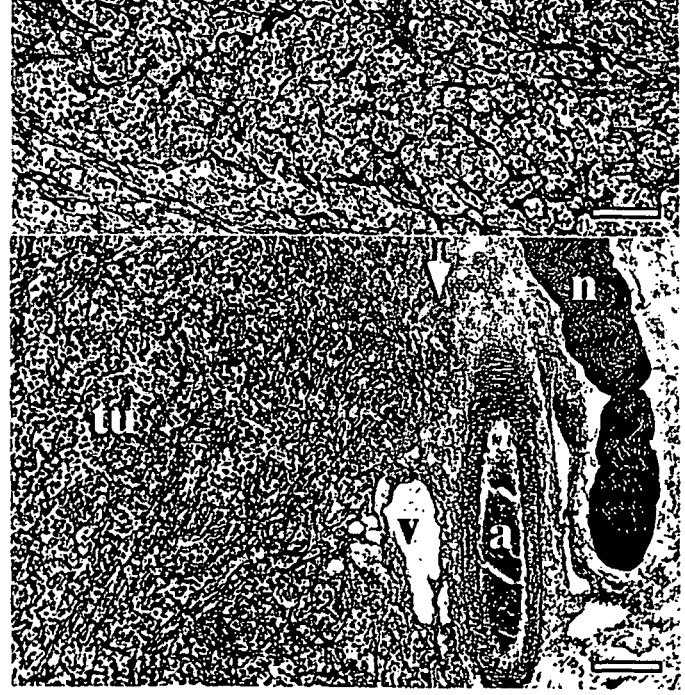

Eighty-two days after the intramuscular injection of undifferentiated human embryonic stem cells (H-9.1 clone) into the hindlimb musculature of SCID/beige mice, typical nodules appeared and increased in size progressively as has been previously described (Amit et al., ibid). Stained sections of such nodules reveal them to be teratomas, containing numerous and varied complex differentiated structures as has been previously reported (Thomson et al, *Science* 282, 1145-7, 1998). Injection of $10^6$ HEY-GFP cells at day 61 into such teratomas in SCID/beige mice (FIG. 1) yielded a different gross morphologic appearance compared to the direct hindlimb intramuscular injection of an equal aliquot of HEY-GFP cells. In the case of direct intramuscular injection of tumor cells, the well-described appearance of small nodules at each injection site was observed, in which there was poor demarcation of the nodule from the surrounding murine muscle tissue, and a markedly hemorrhagic surface. In contrast, following injection of an equal aliquot of cells at day 61 into the teratoma, the teratoma surface appeared well circumscribed with relatively few blood vessels and absence of hemorrhage. HEY-GFP cells were injected into the teratomas and stained sections with Gomori technique for reticulin fibers (Gomori, Am. J Path. 13, 993, 1937) was utilized to detect the histochemical appearance of the mixed teratoma structures obtained 21 days after injection of HEY-GFP cells into these teratomas. Histologic appearance at lower power magnification revealed these mixed structures to be comprised of regions with the typical appearance of teratomas derived from human embryonic stem cells with a variety of mature differentiated structures (FIG. 2A), regions of tumor cells with the appearance of a homogeneous mass of cells with the characteristic morphology of adenocarcinoma (FIG. 2B) and also exhibiting high proliferative capacity as exhibited by the number of cells in mitosis and by PCNA staining (data not shown), as well as boundary regions in which tumor cells appeared adjacent to differentiated teratoma structures such as the neurovascular bundle shown in FIG. 2C.

Example 3

Tumor Cell Invasion into Normal Tissue

Figure 3A:
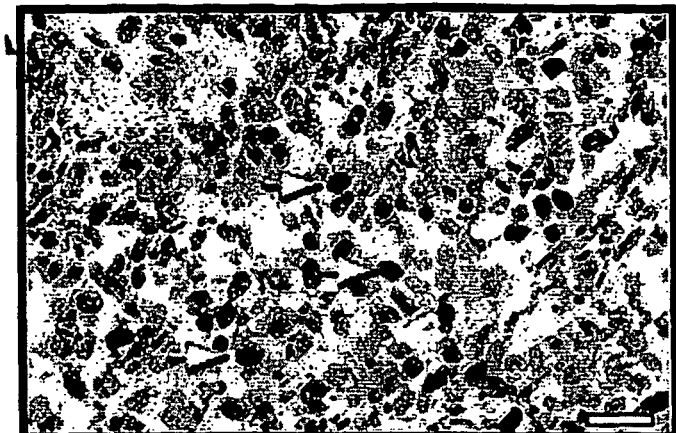
FIG. 3 shows infiltration of HEY-GFP cells into human teratoma derived tissue: (A) arrows indicate HEY-GFP positive nuclear immunostaining of HEY-GFP cells in a field of tumor cells (Bar=50 µm); (B) and (C) arrows indicate migration of tumor (tu) derived GFP positive cells into the teratoma (te) derived adipocytes (ad) and crossing adjacent nerve tissue (n, (Bar=50 µm); (D) arrows indicate invasion of HEY-GFP positive cells into the surrounding connective tissue (Bar=50 µm); (E) enlargement of inset from D (Bar=20 µm); and (F) invasion of tumor derived GFP positive cells into surrounding mouse muscle cells following direct intramuscular injection (Bar=50 µm).
Figure 3B:
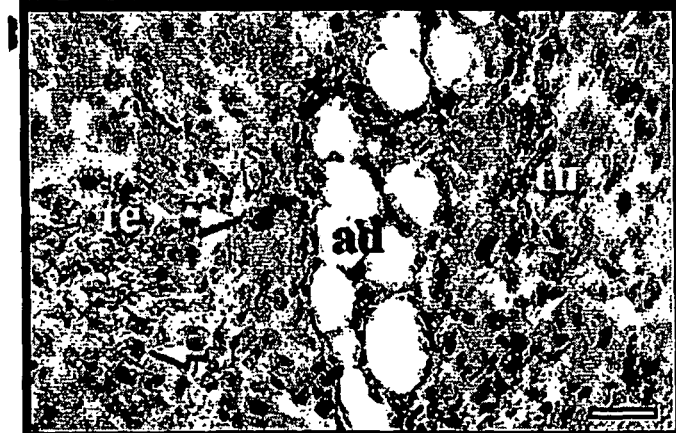
Figure 3C:

Since invasiveness is a hallmark characteristic of tumorigenesis, and because of the appearance of tumor cells adjacent to human ES derived teratoma structures, we sought to track the possible migration and infiltration of tumor cells into normal differentiated tissue. For this purpose, since the HEY-GFP cells are stably transfected to constitutively express GFP, it was possible to track HEY-GFP cell infiltration using immunohistochemistry for GFP. FIG. 3A shows nuclear GFP positive immunohistochemical staining in a field of tumor cells. Although there is variable intensity of staining, positive staining is easily detectable in tumor cell nuclei. FIG. 3B-E show GFP positive cells, which have invaded and interspersed among teratoma-derived differentiated cells and structures such as adipocytes and migrated to the other side of a neural structure (FIGS. 3B,C) or surrounding connective tissue (FIGS. 3D,E). In the case of nodules generated by direct intramuscular injection of HEY-GFP ovarian cancer cells in SCID/beige mice, there is expected invasion of GFP positive cells into the surrounding murine muscle tissue (FIG. 3F).

Example 4

Tumor Induced Angiogenesis in Teratoma Host Tissue

Growth of tumor-derived nodules in immunocompromised mouse models, has been extensively used to demonstrate tumor angiogenesis, which is considered crucial for tumor growth. Blood vessels of murine origin have been shown to grow within the tumor nodules, and anti-angiogenic agents have been shown to disrupt this effect and induce tumor regression in such experimental models.

In order to determine whether tumors growing within hES-derived teratomas would elicit the growth of teratoma-derived blood vessels of human origin adjacent to and within the tumor endothelial marker antibodies were used. Specific markers were used for mouse and for human blood vessels, i.e. the CD34 and CD31 human and mouse specific surface endothelial marker antibodies respectively, enabling to distinguish between these two types of blood vessels.

Figure 4A:
FIG. 4 exhibits detection of tumor neo-angiogenesis using human specific CD34 antibodies: (A) a specimen of human breast carcinoma stained with anti CD34 human specific antibody as a positive control: (Bar=50 µm); (B) photomicrographs showing low power magnifications of CD34 positive immunostaining of an arteriole adjacent to a mass of HEY tumor cells growing within a human teratoma (Bar=100 µM); (C) higher-power magnification of the inset from B demonstrating specificity of staining of the endothelial cell layer. (Bar=20 µm); (D-F) additional human CD34 positively staining blood vessels adjacent to and within tumor cells. [a: arteriole, v: venule, bv: blood vessel, tu: tumor]. (Bar=50 µm for panel D, Bar=100 µm for panel E and Bar=50 µm for panel F).
Figure 4B:
Figure 4C:
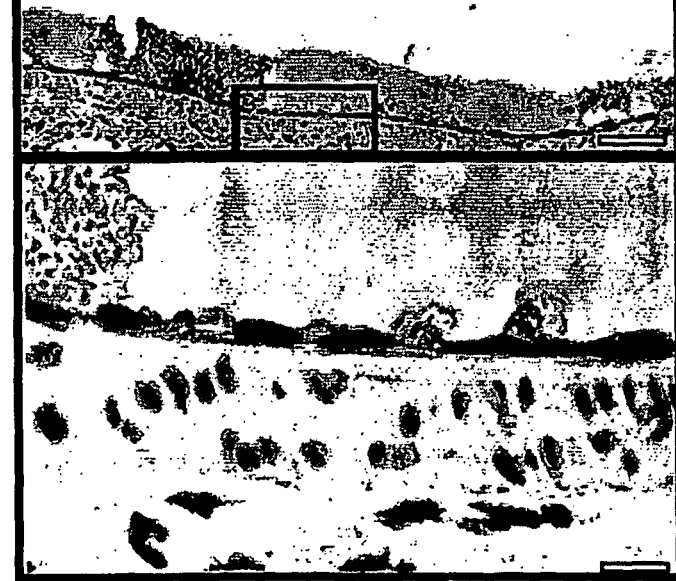
Figure 4D:
Figure 4E:
Figure 4F:
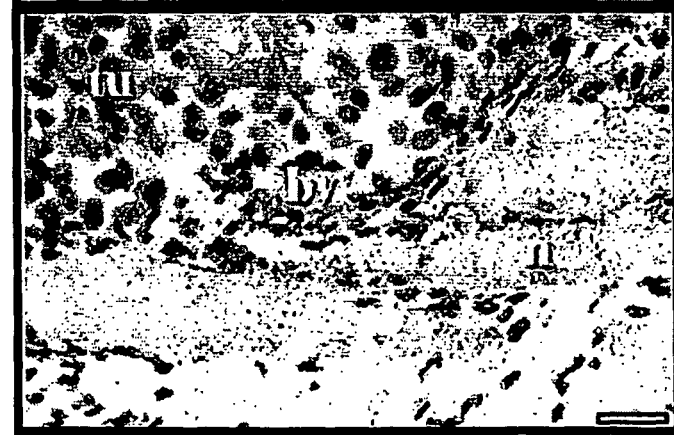
Figure 5A:
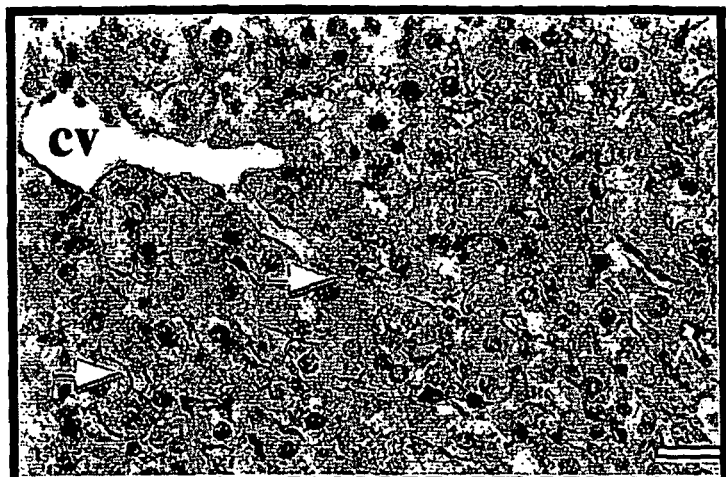
FIG. 5 presents photomicrographs of mouse-specific CD31 immunostaining: (A) normal mouse hepatic sinusoidal endothelium stained with anti-CD31 mouse specific antibody as positive control. [cv: central hepatic vein (Bar=50 µm); (B) mouse specific anti-CD31 immunostaining of blood vessels in a tumor nodule following direct intramuscular injection (Bar=50 µm); and (C) absence of signal in mouse specific anti-CD31 antibody stained section containing a neurovascular structure (Bar=50 µm).
Figure 5B:
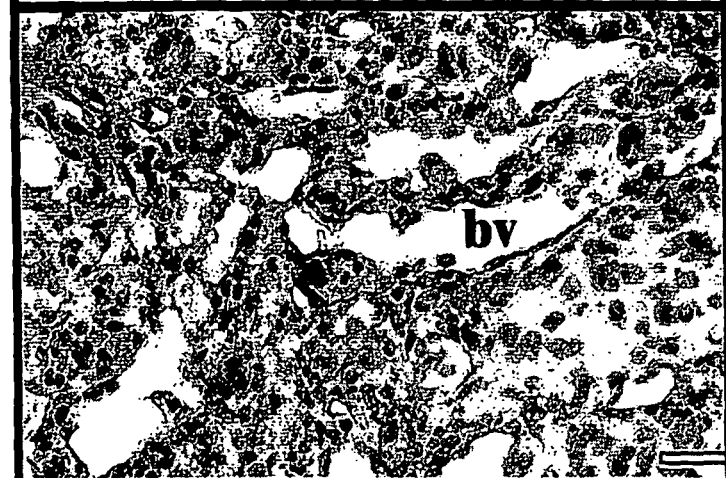
Figure 5C:
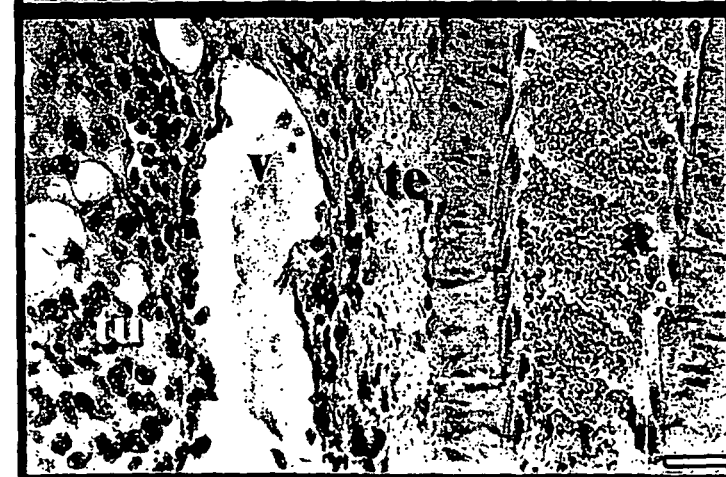

FIG. 4A shows a positive control of immunostaining with human specific CD34 antibody of blood vessels in a specimen of human breast carcinoma. FIGS. 4B and C are photomicrographs showing low- and higher-power magnifications of CD34 positive immunostaining of an arteriole adjacent to a mass of HEY tumor cells growing within a human teratoma. Specificity of staining of the endothelial cell layer is evident in the higher power magnification. FIG. 4D-F show a variety of additional human CD34 positively staining blood vessels of various sizes and configuration (arteriole, venule, capillary and immature small blood vessel characteristic of tumor-induced angiogenesis), adjacent to and within tumor cells. Hepatic sinusoid endothelium immunostained by mouse specific CD31 antibody is shown in normal mouse liver tissue (FIG. 5A), and in a HEY-derived tumor nodule following direct intramuscular injection in SCID/beige mice (FIG. 5B). In contrast, mouse-specific CD31 immunostaining is not evident in HEY ovarian cancer-derived cells growing within an hES teratoma, despite the presence of blood vessels adjacent to and within the tumor mass (FIG. 5C).

Thus, human ovarian cancer cells elicit a neo-angiogenic response, which is of murine origin in the case of tumors growing directly within the surrounding murine tissue, and of human origin in the case of growth within normal differentiated human tissue of embryonic stem cell origin. Other blood vessels within the teratoma tissue itself were stained either with CD31 or with CD34 reflecting neo-angiogenesis of murine origin at early stages of teratoma generation in the mouse and subsequent differentiation of human ES cells into blood vessels of human cellular origin, and did not differ in appearance between control versus tumor-injected teratomas.

Example 5

Multicellular Compositions Comprising Non-Ovarian Cancer Cell Lines

In order to demonstrate that the experimental model is applicable to a wide variety of tumor cell lineages, we have modified several tumor cell lines so as to constitutively express GFP-H2A driven by the CMV promoter. Among these cell lines are A431 (cervical squamous epidermoid carcinoma), PC3 and LNCap1740 (prostate carcinoma cell lines).

These cell lines were shown to generate nodules in SCID/beige mice. The A431 cell line was also injected into hES derived teratomas and we have already demonstrated tumor generation within the human cellular microenvironment. The A431 tumor line is characterized by a very high degree of neoangiogenesis and will be used also in specific aim 1.4 and in experiments involving anti angiogenic factors in specific aim 2.2.

In addition specific antibodies will be used in these teratomas to identify tumor cells as follow: A431 tumor cells will be detected using anti-EGF receptor antibody, which is highly expressed in these cells. Prostate-specific membrane antigen (PSA) will be used in teratomas containing tumors derived from injection of prostate carcinoma cell lines.

We have injected 2×10⁶ A431 cells (epidermoid carcinoma cell line), 3×10⁶ PC3 cells (prostate cancer cell line) and 3×10⁶ LNCap cells (prostate cancer cell line) into established teratomas that were developed IM in SCID/beige mice following injection of hES cells. All three cancer cell lines stably express a fusion protein comprised of enhanced green fluorescence protein EGFP and hisone H2A that is expressed in the cell nuclei.

Teratomas bearing A431 cells were harvested 10 days following injection of cancer cells. Teratomas bearing PC3 and LNCap cells were harvested 37 days following injection. Paraffin sections of harvested teratomas stained with hematoxylin/eosin reveal a homogenous mass of tumor cells within the characteristic differentiated structures of the teratomas. Within the mass of tumor cells a high number of cells in mitosis and a large amount of small blood vessels can be observed. More established blood vessels could be observed at the boundary regions between the tumor and the teratomas. Tumor cells were identified using immunohistochemistry (IHC) with anti GFP antibody.

Tumors derived from injection of A431 cells that express high levels of EGFR exhibited overlapping staining of tumor cells with anti GFP antibody and anti EGFR antibody.

Tumors derived from injection of PC3 cells or LNCap cells that express high levels of PSA (prostate specific antigen) exhibited overlapping staining of tumor cells with anti GFP antibody and anti PSA antibody.

In the case of A431, invasion and migration of tumor cells into the teratoma tissue and generation of new nodules as a result of this migration in the teratomas tissue are highly observed following staining with anti GFP and anti EGFR antibodies.

As mentioned above A431 tumor line is characterized by a very high degree of neoangiogenesis. To distinguish mouse-derived from human-derived blood vessels, we performed IHC using human-specific Von Wilebrant Factor (vWF), α-Smooth Muscle Actin, CD34 and mouse specific CD31 antibodies. Blood vessels of human origin (teratomas derived) were observed within the teratoma and adjacent to the tumor. Immature small blood vessels of human origin were observed within the tumor characteristic of tumor-induced neoangiogenesis.

The results confirm that the multicellular compositions of the present invention may comprise any cancer cell lineage.

Example 6

Effect of Anti-Cancer Therapies on a Multicellular Composition Comprising Non-Ovarian Cancer Cell Lines The utility of the multicellular compositions of the invention for testing anti-cancer agents and treatments was demonstrated using a recombinant immunotoxin antibody that reacts with the Lewis$^Y$ (Le$^Y$), a well characterized antigen that is highly expressed in many carcinomas. This anti-cancer immunotherapy was shown to exhibit a complete regression of A431 tumors in mice (Reiter Y, 1998, Trends Biotechnol. 16:513-20).

The experimental set up had 6 different groups each containing 5 SCID/beige mice. 5×10⁶ hES cells were injected into the hind limb and teratomas were allowed to develop for 7 weeks. 2×10⁶ A431 cells were injected into the teratomas and allowed to develop into a tumor within the teratomas for 5 days before applying immunotherapy. The different groups were treated as follows:
1. Mice bearing teratomas only.
2. Mice bearing tumor containing teratomas.
3. Mice bearing tumor containing teratomas treated with immunotoxin; 2 μg/100 μl injected into the tail vein 3 times, every other day.
4. Mice bearing teratomas treated with immunotoxin, 2 μg/100 μl, injected into the tail vein 3 times, every other day.
5. Mice bearing teratomas treated with PBS.
6. Mice bearing tumor containing teratomas treated with PBS.

For comparison (control), A431 cells were injected directly into the hind limb of SCID/beige mice, and received the same treatments as the teratomas.

Two days following the last treatment, all mice were sacrificed, teratomas were harvested and subjected to routine wax embedding procedure for histological examination. Six micrometer paraffin sections were stained with hematoxylin/eosin or subjected to IHC using anti GFP and anti EGFR to detect tumor cells within the teratomas.

Direct injection of A431 cells into the mouse hind-limb resulted in development of control tumors which exhibited a high degree of angiogenesis. Tumor cells were GFP and EGFR positive using Immunohistochemistry (IHC). Blood vessels within the tumor were positively stained for mouse specific CD31 antibody, and negative for human specific vWF, α-Smooth Muscle Actin and CD34 antibodies. Injection of immunotoxin trough the tail vein resulted in complete regression as observed by palpation. Histological examinations revealed a small remnant of unviable tumor cells with small and condensed nuclei that were negatively stained for EGFR.

Histologic appearance of tumor bearing teratomas without treatment and tumor bearing teratomas treated with PBS, revealed that the tumor cells developed into a homogenous mass of cells with characteristic morphology of abnormal carcinoma. Tumor cells exhibited high proliferative capacity at tumors periphery. Tumor cells that invaded into the normal surrounding microenvironment were also detected, as indicated by GFP and EGFR positive cells interspersed among teratomas derived connective tissue, adipocytes, lamina propria tissue and neurovascular bundles. New foci of viable tumor cells were also observed.

Upon immunotherapy a complete regression of tumor growth within the teratomas was demonstrated. However small foci (100 μm-600 μm) of viable tumor cells, were observed suggesting that a longer immunotherapy treatment and/or addition of another treatment (e.g. with anti-angiogenic factors) would completely eliminate tumor cells from the teratomas.

IHC of sections derived from teratomas bearing tumors, in the presence or absence of immunotoxin treatment, stained with human specific vWF, α-Smooth Muscle Actin and CD34 antibodies revealed the existence of established and immature small blood capillaries of human origin within the multicellular complex of teratomas and the cancer cells.

Example 7

Magnetic Resonance (MRI) Analysis of Multicellular Compositions in Vivo

The following models were incorporated in the MRI experiments:
Mice bearing tumors;
Mice bearing teratomas; and
Mice bearing tumor within a teratoma.

Tumor tissue appeared homogenous compared to the teratomas tissue due to the existence of different differentiated structures. MRI analysis also indicated that the tumors which developed directly in the hind-limb of the mice exhibits a higher degree of angiogenesis as compared to tumors developed within a teratoma.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the scope of the invention.

The invention claimed is:

1. A three-dimensional multicellular composition comprising isolated human cancer cells within a microenvironment of nonmalignant human cells that are human embryonic stem cells (hESC) in the form of an embryoid body or a teratoma, wherein the embryoid body or teratoma has a three-dimensional structure with the human cancer cells being within and surrounded by the embryoid body or teratoma, and wherein the cancer cells are cells from an established cell line or from a primary clinical sample and maintain their abnormal phenotype.

2. The multicellular composition of claim 1, wherein the nonmalignant human cells are human embryonic stem cells in the form of an embryoid body and said human cancer cells are within the embryoid body.

3. The multicellular composition of claim 1, comprising human cancer cells disposed within a teratoma.

4. The multicellular composition of claim 1, maintained in culture.

5. The multicellular composition of claim 1, maintained within a non-human host animal.

6. The multicellular composition of claim 5, maintained at a defined predetermined site within the non-human host animal.

7. The multicellular composition of claim 5, maintained intraperitoneally in ascites form.

8. The multicellular composition of claim 5, wherein said multicellular composition is a teratoma.

9. The multicellular composition of claim 1, occluded within a barrier membrane.

10. The multicellular composition of claim 9, maintained at a defined predetermined site within a non-human host animal.

11. The multicellular composition of claim 1, in which the cancer cells have invaded the microenvironment of nonmalignant human cells.

12. The multicellular composition of claim 1, in which the cancer cells have induced angiogenic activity in the microenvironment of nonmalignant human cells.

13. The multicellular composition of claim 1, in which the cancer cells have elicited formation of new human blood vessels within the microenvironment of nonmalignant human cells.

14. The multicellular composition of claim 1, wherein at least some cells in the multicellular composition comprise at least one exogenous polynucleotide.

15. The multicellular composition of claim 14, wherein the at least one exogenous polynucleotide is within a vector.

16. The multicellular composition of claim 15, wherein the vector is a plasmid or a virus.

17. The multicellular composition of claim 16, wherein the vector is a virus selected from the group consisting of adenoviruses, retroviruses and lentiviruses.

18. The multicellular composition of claim 14, wherein the at least one exogenous polynucleotide is stably integrated into the genome of the at least some cells in the multicellular composition.

19. The multicellular composition of claim 14, wherein the at least one exogenous polynucleotide is transiently expressed by the at least some cells in the multicellular composition.

20. The multicellular composition of claim 14, wherein the at least one exogenous polynucleotide comprises at least one regulatory element.

21. The multicellular composition of claim 20, wherein the at least one regulatory element is selected from the group consisting of promoter, enhancer, post transcriptional element, initiation codon, stop codon, polyadenylation signal and selection marker.

22. The multicellular composition of claim 14, wherein the at least one exogenous polynucleotide is operably linked to expression control sequences.

23. The multicellular composition of claim 1, wherein the cancer cells are transfected with a marker gene.

24. The multicellular composition of claim 1, wherein the cancer cells are stably transfected with a marker gene.

25. The multicellular composition of claim 23, wherein the marker is selected from the group consisting of nuclear histone H2A-green fluorescent fusion protein and red fluorescence fusion protein with nuclear localization signal.

26. The multicellular composition of claim 1, wherein the cancer cells are derived from solid malignant tumors, non-solid malignant tumors, or hematologic cancers.

27. The multicellular composition of claim 26, wherein the cancer cells are selected from the group consisting of prostate cancer, breast cancer, ovarian cancer, lung cancer, melanoma, renal cancer, bladder cancer, fibrosarcoma, hepatocellular carcinoma, osteocarcinoma, primary ductal carcinoma, giant cell sarcoma, ductal carcinoma, Hodgkin's disease, colorectal carcinoma, leukemia, lymphoma, transitional cell carcinoma, uterine sarcoma, adenocarcinoma, plasmacytoma, epidermoid carcinoma, Burkitt's lymphoma, Ewing's sarcoma, gastric carcinoma, squamous cell carcinoma, neuroblastoma and rhabdomyosarcoma.

28. A method of producing the multicellular composition according to claim 1, comprising introducing the human cancer cells into a microenvironment of the nonmalignant human cells.

29. The method according to claim 28, comprising:
 (a) culturing hESC in conditions which promote formation of embryoid bodies, thereby forming at least one embryoid body;
 (b) injecting human cancer cells into the at least one embryoid body, thereby obtaining at least one multicellular composition in which the cancer cells are within and surrounded by the cells of the embryoid body.

30. The method according to claim 29, further comprising injecting said at least one multicellular composition into a non-human host animal.

31. The method according to claim 30, wherein said at least one multicellular composition is injected into a site in the non-human host animal selected from the group consisting of a defined predetermined locus and the peritoneal cavity.

32. The method according to claim 29, further comprising:
 (c) occluding said at least one multicellular composition within a barrier membrane; and (d) implanting said at least one multicellular composition into a non-human host animal.

33. The method according to claim 28, comprising:
(a) injecting undifferentiated human embryonic stem cells into a non-human host animal;
(b) determining the formation of at least one teratoma in the locus of injection;
(c) injecting human cancer cells into the at least one teratoma of (b), thereby obtaining at least one multicellular composition in which the human cancer cells are within and surrounded by the teratoma.

34. The method according to claim 33, wherein the undifferentiated human embryonic stem cells are injected into a site of the non-human host animal selected from the group consisting of a defined locus and the peritoneal cavity.

35. The method according to claim 28, wherein the human cancer cells are cells from an established cell line or from a primary clinical sample.

36. The method according to claim 30, wherein the non-human host animal is immunodeficient.

37. The method according to claim 28, wherein the human cancer cells are derived from solid malignant tumors, non-solid malignant tumors, or hematologic cancers.

38. The method according to claim 28, wherein the human cancer cells are selected from the group consisting of prostate cancer, breast cancer, ovarian cancer, lung cancer, melanoma, renal cancer, bladder cancer, fibrosarcoma, hepatocellular carcinoma, osteocarcinoma, primary ductal carcinoma, leukemia, giant cell sarcoma, ductal carcinoma, Hodgkin's disease, colorectal carcinoma, lymphoma, transitional cell carcinoma, uterine sarcoma, adenocarcinoma, plasmacytoma, epidermoid carcinoma, Burkitt's lymphoma, Ewing's sarcoma, gastric carcinoma, squamous cell carcinoma, neuroblastoma, and rhabdomyosarcoma.

39. The multicellular composition of claim 1, wherein the nonmalignant human cells are pluripotent human embryonic stem cells cultured on a three-dimension polymer-based model.

* * * * *